(12) United States Patent
Hoarau et al.

(10) Patent No.: US 9,848,870 B2
(45) Date of Patent: Dec. 26, 2017

(54) COUPLING SYSTEM, APPLICATOR TOOL, ATTACHMENT RING AND METHOD FOR CONNECTING A CONDUIT TO BIOLOGICAL TISSUE

(71) Applicants: Carine Hoarau, Lafayette, CA (US); Steven H. Reichenbach, Pleasanton, CA (US); J. Donald Hill, San Francisco, CA (US); George Hsu, San Ramon, CA (US); Andrew R. Miller, The Woodlands, TX (US); James Badia, Redwood City, CA (US); Nina Boiadjieva, Belmont, CA (US); Shuo-Hsiu Chang, Fremont, CA (US); Philip Haarstad, Chanhassen, MN (US); Olga M. Stanescu, San Jose, CA (US); Stephen Kenneth Sundquist, Minnetonka, MN (US)

(72) Inventors: Carine Hoarau, Lafayette, CA (US); Steven H. Reichenbach, Pleasanton, CA (US); J. Donald Hill, San Francisco, CA (US); George Hsu, San Ramon, CA (US); Andrew R. Miller, The Woodlands, TX (US); James Badia, Redwood City, CA (US); Nina Boiadjieva, Belmont, CA (US); Shuo-Hsiu Chang, Fremont, CA (US); Philip Haarstad, Chanhassen, MN (US); Olga M. Stanescu, San Jose, CA (US); Stephen Kenneth Sundquist, Minnetonka, MN (US)

(73) Assignee: THORATEC CORPORATION, Pleasanton, CA (US)

( * ) Notice: Subject to any disclaimer, the term of this patent is extended or adjusted under 35 U.S.C. 154(b) by 311 days.

(21) Appl. No.: 14/808,350

(22) Filed: Jul. 24, 2015

(65) Prior Publication Data

US 2015/0343124 A1 Dec. 3, 2015

Related U.S. Application Data

(62) Division of application No. 13/406,511, filed on Feb. 27, 2012, now Pat. No. 9,125,648.
(Continued)

(51) Int. Cl.
*A61B 17/10* (2006.01)
*A61B 17/064* (2006.01)
(Continued)

(52) U.S. Cl.
CPC .......... *A61B 17/064* (2013.01); *A61B 17/072* (2013.01); *A61B 17/07292* (2013.01);
(Continued)

(58) Field of Classification Search
CPC ...... A61B 2017/00867; A61B 17/0644; A61B 17/064; A61B 2017/0649; A61B 17/068;
(Continued)

(56) References Cited

U.S. PATENT DOCUMENTS

| 5,158,563 A | 10/1992 | Cosman |
| 5,291,179 A | 3/1994 | Ooe et al. |

(Continued)

FOREIGN PATENT DOCUMENTS

| DE | 10 2004 047974 | 4/2006 |
| EP | 0 957 775 | 4/2009 |

(Continued)

OTHER PUBLICATIONS

"Radial" definition from Merriam-Webster accessed Sep. 26, 2014.
(Continued)

*Primary Examiner* — Katherine M Shi
(74) *Attorney, Agent, or Firm* — Squire Patton Boggs (US) LLP

(57) ABSTRACT

A coupling system includes an applicator tool and an attachment ring mounted on the applicator tool. Clips are contained within the applicator tool and are deployed through the attachment ring in order to anchor the attachment ring to biological tissue. When deployed, tips of the clips follow a curved trajectory through an annular cuff of the attachment ring and through the underlying tissue. The tips loop back out of the tissue and to a location where they are later trapped or clamped by the attachment ring. While the tips are trapped or clamped, the applicator tool cinches the clips by pulling rear segments of the clips. Thereafter, the applicator tool disconnects from the attachment ring which remains anchored to the tissue and serves as a coupling for a cannula. The cannula can have movable lock members that secure it to the attachment ring.

17 Claims, 32 Drawing Sheets

Related U.S. Application Data

(60) Provisional application No. 61/446,996, filed on Feb. 25, 2011, provisional application No. 61/603,140, filed on Feb. 24, 2012.

(51) Int. Cl.
  *A61B 17/072* (2006.01)
  *A61M 1/10* (2006.01)
  *A61B 17/115* (2006.01)
  *A61M 1/12* (2006.01)
  *A61B 17/04* (2006.01)
  *A61B 17/00* (2006.01)
  *A61B 17/11* (2006.01)

(52) U.S. Cl.
  CPC .......... *A61B 17/10* (2013.01); *A61B 17/1155* (2013.01); *A61M 1/1008* (2014.02); *A61M 1/1087* (2014.02); *A61M 1/1096* (2014.02); A61B 2017/00867 (2013.01); A61B 2017/0441 (2013.01); *A61B 2017/0443* (2013.01); *A61B 2017/0647* (2013.01); *A61B 2017/0649* (2013.01); *A61B 2017/1107* (2013.01); *A61M 1/101* (2013.01); *A61M 1/1098* (2014.02); *A61M 1/122* (2014.02)

(58) Field of Classification Search
  CPC ........ A61B 17/0057; A61B 2017/0641; A61B 17/11; A61B 17/1227; A61B 2017/00243; A61B 2017/0647; A61B 2017/1107; A61B 17/0401; A61B 2017/00575; A61B 2017/00668; A61B 2017/00592; A61B 2017/1135; A61B 17/072; A61B 17/083; A61B 17/115; A61B 17/1285; A61B 2017/00579; A61F 2/2466; A61F 2220/0016
  USPC ....... 606/139, 142, 143, 151, 153, 157, 213, 606/219; 227/175.1, 178.1, 901, 902, 227/176.1, 180.1
  See application file for complete search history.

(56) References Cited

U.S. PATENT DOCUMENTS

| | | |
|---|---|---|
| 5,582,616 A | 12/1996 | Bolduc et al. |
| 5,814,005 A | 9/1998 | Barra et al. |
| 5,827,316 A | 10/1998 | Young et al. |
| 6,079,414 A | 6/2000 | Roth |
| 6,080,173 A | 6/2000 | Williamson, IV et al. |
| 6,113,611 A | 9/2000 | Allen et al. |
| 6,193,652 B1 | 2/2001 | Berry et al. |
| 6,346,071 B1 | 2/2002 | Mussivand |
| 6,402,765 B1 | 6/2002 | Monassevitch et al. |
| 6,537,300 B2 | 3/2003 | Girton |
| 6,551,332 B1 | 4/2003 | Nguyen et al. |
| 6,607,541 B1 | 8/2003 | Gardiner et al. |
| 6,669,708 B1 | 12/2003 | Nissenbaum et al. |
| 6,689,147 B1 | 2/2004 | Koster, Jr. |
| 6,695,859 B1 | 2/2004 | Golden et al. |
| 6,699,256 B1 | 3/2004 | Logan et al. |
| 6,726,648 B2 | 4/2004 | Kaplon et al. |
| 6,732,501 B2 | 5/2004 | Yu et al. |
| 6,802,806 B2 | 10/2004 | McCarthy et al. |
| 6,824,071 B1 | 11/2004 | McMichael |
| 6,863,677 B2 | 3/2005 | Breznock |
| 6,942,672 B2 | 9/2005 | Heilman et al. |
| 7,077,801 B2 | 7/2006 | Haverich |
| 7,309,343 B2 | 12/2007 | Vargas et al. |
| 7,510,561 B2 | 3/2009 | Beane et al. |
| 7,717,844 B2 | 5/2010 | Cohn |
| 7,744,527 B2 | 6/2010 | Cohn |
| 7,846,123 B2 | 12/2010 | Vassiliades et al. |
| 7,931,581 B2 | 4/2011 | Cohn |
| 7,942,805 B2 | 5/2011 | Shambaugh, Jr. |
| 7,993,392 B2 | 8/2011 | Righini et al. |
| 2002/0045846 A1 | 4/2002 | Kaplon et al. |
| 2003/0023255 A1 | 1/2003 | Miles et al. |
| 2003/0078604 A1 | 4/2003 | Walshe |
| 2003/0130668 A1 | 7/2003 | Nieman et al. |
| 2004/0049194 A1 | 3/2004 | Harvie et al. |
| 2004/0092798 A1 | 5/2004 | Spence et al. |
| 2004/0102794 A1 | 5/2004 | Roy et al. |
| 2004/0138744 A1 | 7/2004 | Lashinski et al. |
| 2004/0243154 A1 | 12/2004 | Berg et al. |
| 2004/0249398 A1 | 12/2004 | Ginn |
| 2005/0080437 A1 | 4/2005 | Wright |
| 2005/0187568 A1 | 8/2005 | Klenk et al. |
| 2005/0251209 A1 | 11/2005 | Saadat et al. |
| 2006/0036313 A1 | 2/2006 | Vassiliades et al. |
| 2006/0074484 A1 | 4/2006 | Huber |
| 2006/0089707 A1 | 4/2006 | Vassiliades et al. |
| 2006/0142789 A1 | 6/2006 | Lehamn et al. |
| 2006/0167333 A1 | 7/2006 | Moore et al. |
| 2006/0253143 A1 | 11/2006 | Edoga et al. |
| 2007/0055357 A1 | 3/2007 | Pokorney et al. |
| 2007/0066943 A1 | 3/2007 | Prasad et al. |
| 2007/0106315 A1 | 5/2007 | Gregoric et al. |
| 2007/0112384 A1 | 5/2007 | Conlon et al. |
| 2007/0167969 A1 | 7/2007 | Pandey |
| 2007/0197856 A1 | 8/2007 | Gellman et al. |
| 2007/0225642 A1* | 9/2007 | Houser .............. A61B 17/0644 604/93.01 |
| 2007/0265643 A1 | 11/2007 | Beane et al. |
| 2008/0004640 A1 | 1/2008 | Ellingwood |
| 2008/0300628 A1 | 12/2008 | Ellingwood |
| 2009/0112062 A1 | 4/2009 | Bakos |
| 2009/0171136 A1 | 7/2009 | Shambaugh, Jr. |
| 2009/0204206 A1 | 8/2009 | Parquet et al. |
| 2009/0302089 A1 | 12/2009 | Harari et al. |
| 2010/0010500 A1 | 1/2010 | Beane et al. |
| 2010/0010538 A1 | 1/2010 | Juravic et al. |
| 2010/0161040 A1 | 6/2010 | Braido et al. |
| 2010/0168778 A1 | 7/2010 | Braido |
| 2010/0211082 A1 | 8/2010 | Sauer |
| 2011/0087277 A1 | 4/2011 | Viola et al. |
| 2011/0118766 A1 | 5/2011 | Reichenbach et al. |
| 2011/0118829 A1 | 5/2011 | Hoarau et al. |
| 2011/0118833 A1 | 5/2011 | Reichenbach et al. |
| 2012/0089181 A1 | 4/2012 | Shanley et al. |

(56) References Cited

U.S. PATENT DOCUMENTS

2012/0165931 A1 6/2012 Bourque
2012/0296349 A1 11/2012 Smith et al.

FOREIGN PATENT DOCUMENTS

| EP | 1 691 884 B1 | 3/2011 |
|----|---|---|
| EP | 1 628 702 B1 | 5/2013 |
| WO | WO 96/03925 | 2/1996 |
| WO | WO 96/25886 | 8/1996 |
| WO | WO 03/001980 | 1/2003 |
| WO | WO 2006/019755 | 2/2006 |
| WO | WO 2007/038109 | 4/2007 |
| WO | WO 2008/153872 A2 | 12/2008 |
| WO | WO 2009/100198 | 8/2009 |
| WO | WO 2013/064529 A1 | 5/2013 |

OTHER PUBLICATIONS

International Search Report and Written Opinion for PCT/US2014/029703, dated Jul. 17, 2014, 14 pgs.
International Search Report for PCT/US2010/056751, dated Oct. 7, 2011, 22 pgs.
International Search Report for PCT/US2012/026838, dated Aug. 10, 2012, 9 pgs.
International Search Report for PCT/US2013/031279, dated Jul. 10, 2013, 14 pgs.

\* cited by examiner

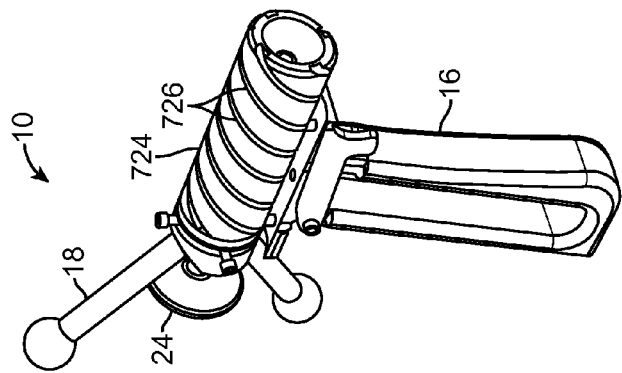
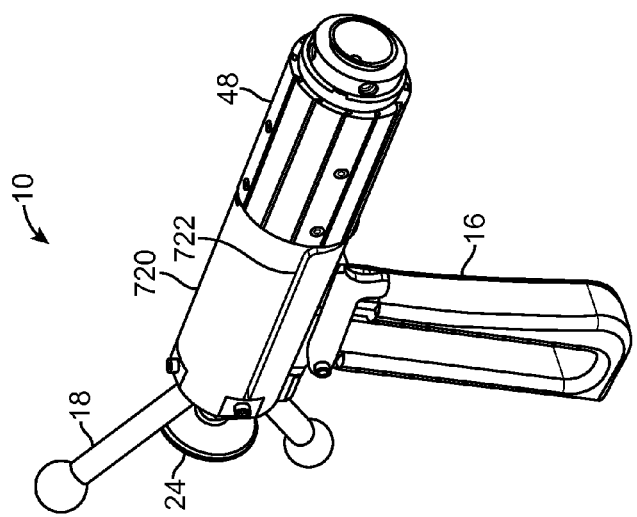
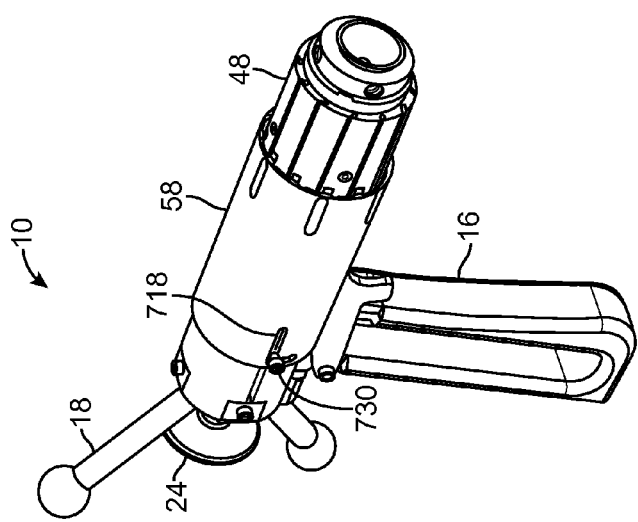

COUPLING SYSTEM, APPLICATOR TOOL, ATTACHMENT RING AND METHOD FOR CONNECTING A CONDUIT TO BIOLOGICAL TISSUE

CROSS-REFERENCE TO RELATED APPLICATIONS

This application is a divisional of U.S. application Ser. No. 13/406,511, filed Feb. 27, 2012, which claims the benefit of U.S. Provisional Application No. 61/446,996, filed Feb. 25, 2011 and U.S. Provisional Application No. 61/603,140, filed Feb. 24, 2012, all of which applications are incorporated herein by reference for all purposes.

FIELD OF THE INVENTION

The invention relates to a coupling system, applicator tool, attachment ring and method for connecting a conduit to biological tissue, and more particularly, for connecting a conduit to the heart.

BACKGROUND OF THE INVENTION

Surgical procedures for connecting a conduit to biological tissue, such as blood vessels and the heart, have required manually suturing the conduit or coupling device to the biological tissue. Manual suturing can be difficult due to limited access to, location of, and/or type of biological tissue. When the procedure is performed on a blood vessel, blood flow may need to be blocked temporarily to avoid the loss of large amounts of blood during the time required for manual suturing and/or to stop pulsatile motion which can make accurate placement of sutures difficult. When the procedure is performed on the heart, the patient is connected to a heart-lung bypass machine and the heart is stopped for a period of time during the procedure.

There is a continuing need to make the procedure for connecting a conduit easier and faster to perform. There is also a need to be able to connect a conduit to the heart, such as during implantation of a ventricular assist device (VAD), with the option of allowing the heart to continue to beat and not having to resort to using a heart-lung bypass machine.

SUMMARY OF THE INVENTION

Briefly and in general terms, the present invention is directed to a coupling system, applicator tool, attachment ring, method, and clip for connecting a prosthesis to biological tissue, and a cannula for attachment to a prosthesis.

In aspects of the present invention, a clip comprises a wire body having a forward segment, a rear segment, and a medial segment connecting the forward segment to the rear segment, the forward segment having a tip configured to pierce biological tissue, the medial segment configured to be elastically deformed to a straight configuration and to autonomously return to a curved configuration from the straight configuration.

In aspects of the present invention, an assembly, for retaining a plurality of clips deployed to connect the assembly to tissue, comprises a main body, a first device, and a second device. The main body is configured to contain a medial segment of each clip. The first device is configured to trap a forward segment of each clip. The second device is configured to cinch each clip while the forward segments of the clips are trapped by the first device.

In aspects of the present invention, a coupling system comprises an applicator tool including a clip tube, a clip pusher, and a clamping tube. The system further comprises a plurality of clips configured for movement within the clip tube by the clip pusher. The system further comprises an implantable attachment device including a cinching ring and a clamping ring, the clamping ring movable relative to the cinching ring by the clamping tube and operable in conjunction with the cinching ring to secure at least one of the clips.

In aspects of the present invention, an attachment ring comprises a main body, an annular cuff, and a clamping ring. The main body includes a cylindrical wall encircling an axial centerline. The annular cuff is attached to the main body. The clamping ring is movable relative to the main body in a direction substantially parallel to the axial centerline. The clamping ring is configured to engage a lock feature on the main body.

In other aspects of the present invention, an applicator tool comprises a plurality of clip holders, a clip pusher, and a connector mechanism. The plurality of clip holders are arranged around an axial centerline, and each clip holder has a clip groove with a slot opening. The clip pusher is configured to move relative to the clip grooves. The connector mechanism is configured to selectively engage onto and disengage from an implantable ring assembly.

In other aspects of the present invention, a cannula comprises a tubular body having a central fluid passageway, and a first lock member biased to move radially outward from the tubular body, the first lock member configured to engage a prosthesis.

In other aspects of the present invention, a method comprises placing an attachment ring on the tissue while the attachment ring is mounted on an applicator tool containing a plurality of clips, followed by anchoring the attachment ring on the tissue. The anchoring includes moving a forward segment of each of the clips in a forward direction out of the applicator tool and through the attachment ring and the tissue, and after the clips are moved through the attachment ring and the tissue, restraining the clips so that a rear segment of each of the clips is capable of one-way movement for cinching the clips.

Various aspects of the invention are directed to a system comprising any of the features described above. Various aspects of the invention are directed to using such a system to connect a prosthesis to biological tissue.

The features and advantages of the invention will be more readily understood from the following detailed description which should be read in conjunction with the accompanying drawings.

BRIEF DESCRIPTION OF THE DRAWINGS

FIGS. 1A-1E are perspective views of an exemplary applicator tool for anchoring an attachment ring to biological tissue using securement clips, the applicator tool shown fully assembled in FIG. 1A, disassembled in FIGS. 1B-1D, and close-up in FIG. 1E.

DETAILED DESCRIPTION OF EXEMPLARY EMBODIMENTS

As used herein, any term of approximation such as, without limitation, near, about, approximately, substantially, essentially and the like mean that the word or phrase modified by the term of approximation need not be exactly that which is written but may vary from that written description to some extent. The extent to which the description may vary will depend on how great a change can be instituted and have one of ordinary skill in the art recognize the modified version as still having the properties, characteristics and capabilities of the modified word or phrase. For example and without limitation, a first structure that is described as "substantially parallel" in reference to a second structure encompasses an orientation that is perfectly parallel and an orientation that one skilled in the art would readily recognize as being parallel even though distances between corresponding locations on the two respective structures are not exactly the same.

As used herein, a "through-hole" refers to a lumen that extends from one surface of a structure completely through the structure to another surface of the structure such that, if desired, a fluid could pass completely through the structure.

Figure 1A:
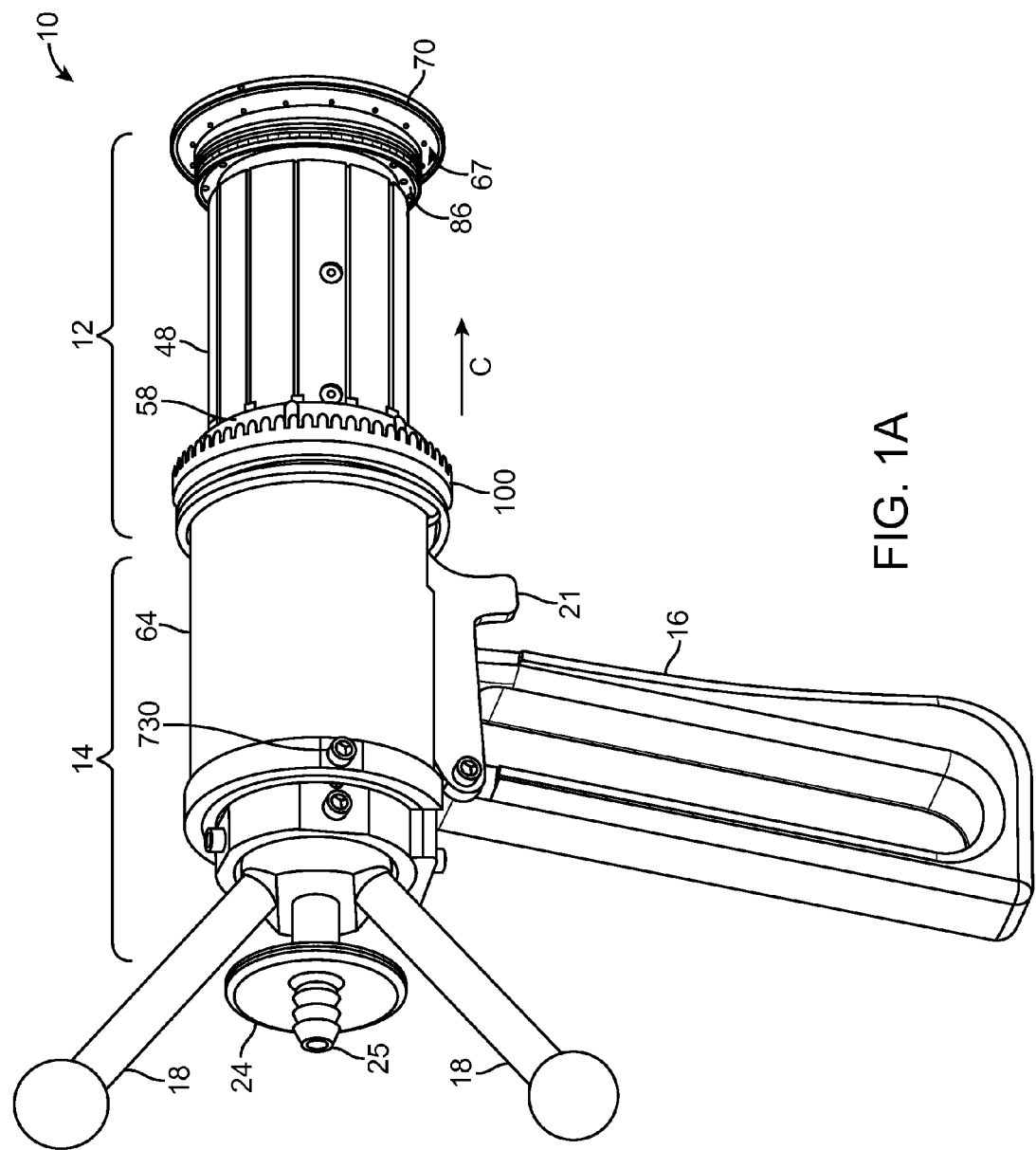
Figure 1E:
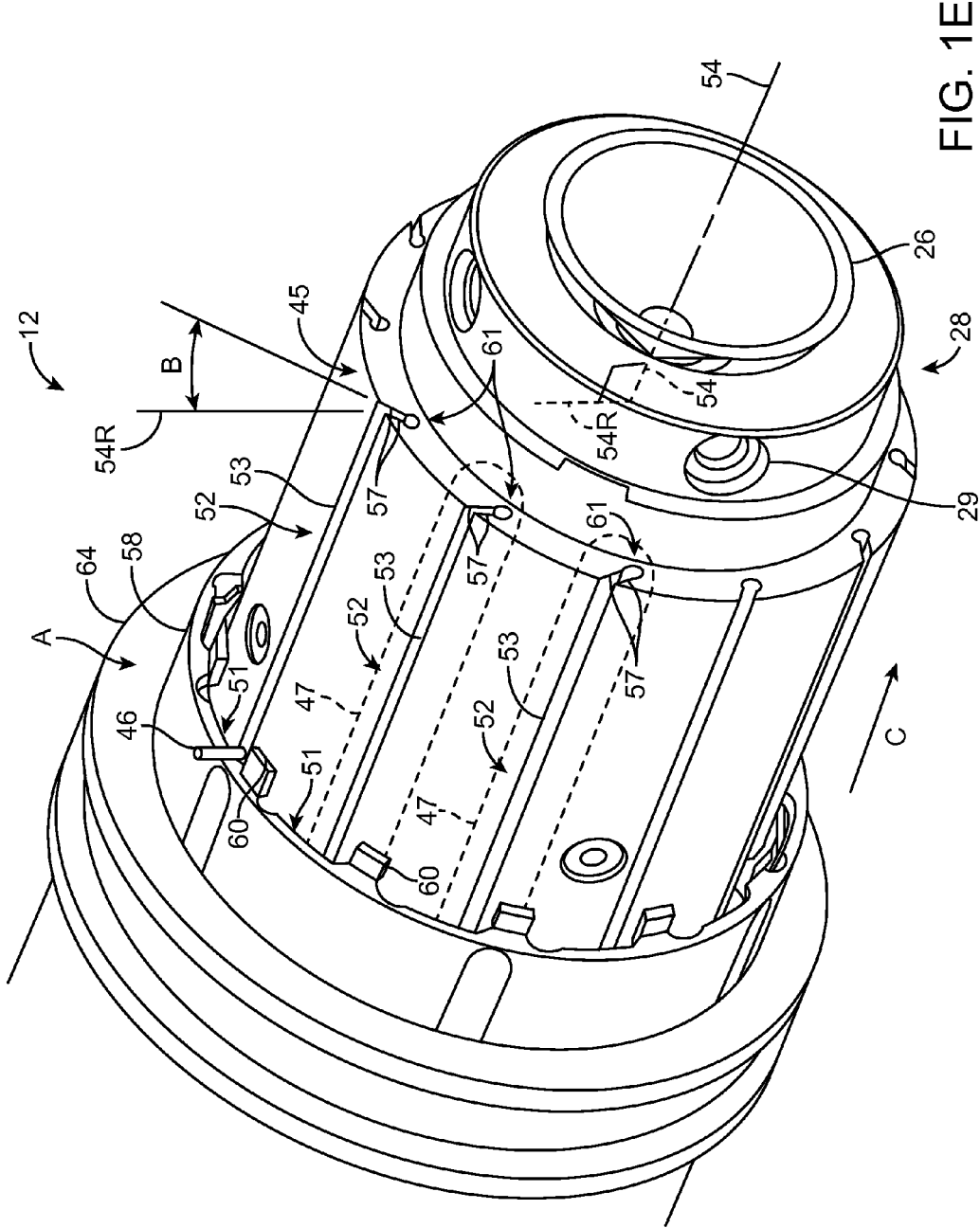

Referring now in more detail to the exemplary drawings for purposes of illustrating exemplary embodiments of the invention, wherein like reference numerals designate corresponding or like elements among the several views, there is shown in FIG. 1A applicator tool 10 for anchoring attachment ring 30 to biological tissue. Although attachment ring 30 is shown and described together with applicator tool 10, it will be appreciated that other applicator tools may be used to anchor attachment ring 30 to biological tissue. FIGS. 1B-1D shows applicator tool 10 without attachment ring 30 and in varying states of disassembly. FIG. 1E shows a detailed view of an exterior portion of applicator tool 10 on which attachment ring 30 could be carried. Exemplary attachment ring 30 is a type of prosthesis suitable for implantation within a human or animal body. Attachment ring 30 is a coupling for a conduit, graft, or other structure that is to be connected to biological tissue. In various embodiments, attachment ring 30 is configured for attaching a device (e.g. a prosthesis, therapy device, a diagnostic device, etc.) to a body lumen or organ. Forward segment 12 of applicator tool 10 is configured to engage attachment ring 30. Rear segment 14 has grip 16. Clip deployment handle 18, clamp release 21, and disengagement knob 24 are used to control various elements in forward segment 12. As described below, clip deployment handle 18 also provides clamping and cinching functions.

Figure 2A:
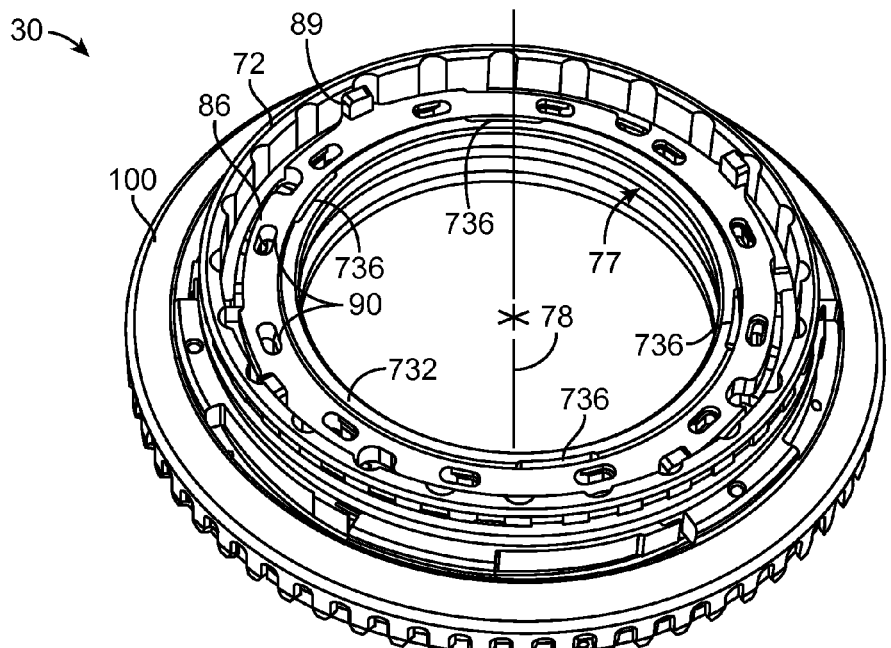
FIGS. 2A-2D are perspective views of an exemplary attachment ring, the attachment ring shown fully assembled in FIGS. 2A-2C (viewed from the top, side, and bottom), and disassembled in FIG. 2D.
Figure 2B:
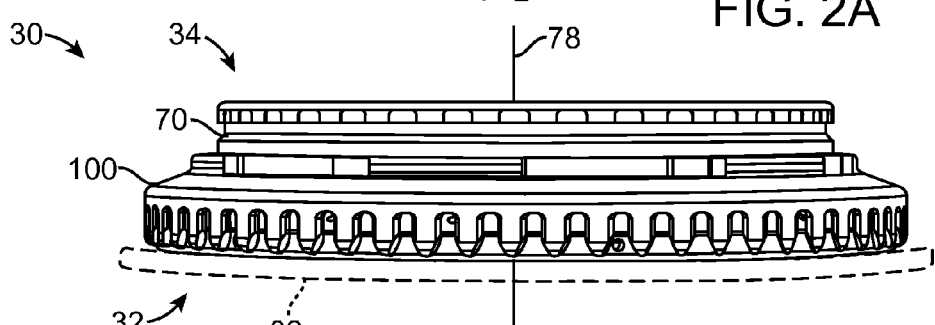
Figure 2C:
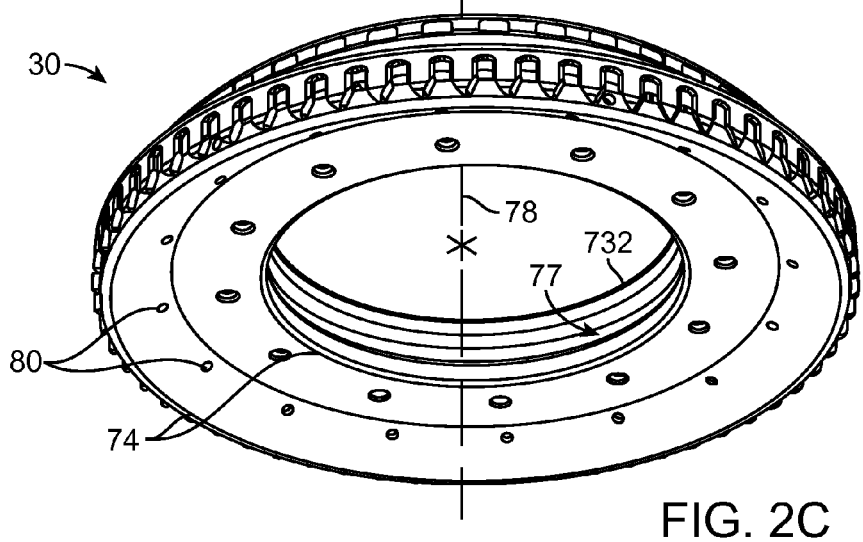
Figure 2D:
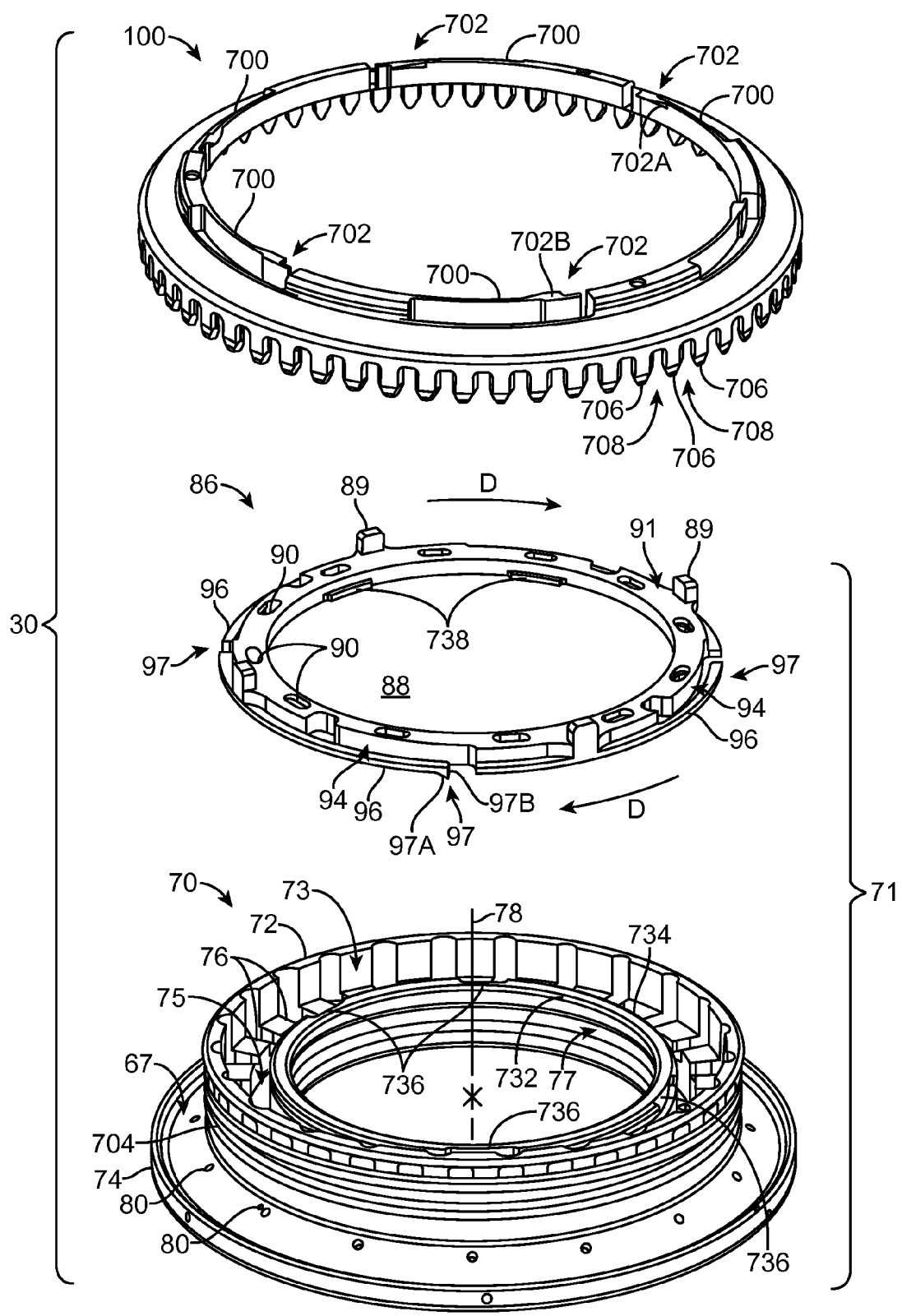

FIGS. 2A-2C show various views of attachment ring 30 in a fully assembled state after completion of clip deployment and clamping processes described below. FIG. 2D shows attachment ring 30 in a disassembled state.

Referring to FIG. 2B, attachment ring 30 has bottom end 32 and top end 34. Bottom end 32 is secured to biological tissue and top end 34 is configured to engage forward segment 12 of applicator tool 10. Attachment ring 30 includes features configured to connect with a conduit, such as an inflow conduit of a ventricular assist device (VAD), after attachment ring 30 has been secured to biological tissue, such as the ventricular apex of the heart. Methods for securing an inflow conduit to the ventricular apex by means of an attachment ring are described in U.S. Application Publication Nos. 2011/0118766 A1, 2011/0118833 A1, and 2011/0118829 A1, which are incorporated herein for all purposes by reference. While the attachment ring and applicator tool will be described in terms of attaching a conduit to a biological tissue such as a body lumen or organ wall, one will appreciate that the devices and methods described herein may be applied equally to a variety of applications.

As shown in FIG. 2D, attachment ring 30 comprises main body 70, cinching ring 86 and clamping ring 100. When used with applicator tool 10, cinching ring 86 is located within main body 70. Main body 70 and cinching ring 86 collectively form ring assembly 71 which is releasably attached to connector mechanism 28 of applicator tool 10. Connector mechanism 28 (FIG. 1E) includes movable lock elements 29 capable of selectively engaging and releasing internal annular groove 77 of attachment ring main body 70. As shown in FIG. 1A, clamping ring 100 is releasably attached to the outer surface of cinching tube 58 and abuts forward end of clamping tube 64 (also referred to as a clamp pusher). In FIG. 1E, clamping ring 100 would be located at a region of applicator tool 10 designated generally by arrow A.

As shown in FIG. 2D, attachment ring main body 70 comprises cylindrical wall 72, ratchet members 76 attached to cylindrical wall 72, and base 74 attached to the bottom of cylindrical wall 72. Main body 70 can be made of titanium, other metal, or other material suitable for implantation within a human or animal body as would be understood by one of skill in the art from the description herein. Cylindrical wall 72 encircles interior space 73. Ratchet members protrude into interior space 73 and face toward axial centerline 78 of cylindrical wall 72. Through-holes 80 are formed through base 74.

Flexible, annular cuff 82 (illustrated in broken line in FIG. 2B) can be attached to base 74 by a suture or thread passing through annular cuff 82 and through-holes 80 of base 74. Annular cuff 82 can be attached to base 74 by an adhesive. Central through-hole of annular cuff 82 is substantially centered upon axial centerline 78. Annular cuff 82 can be made of polytetrafluoroethylene (PTFE) felt, polyethylene terephthalate (PETE) felt, other polyester fibers, titanium, other metals, silicone rubber, any combination thereof, or other material suitable for implantation within a human or animal body as would be understood by one of skill in the art from the description herein. In various embodiments, annular cuff 82 is capable of forming a hemostatic connection with biological tissue when attachment ring 30 is anchored to the biological tissue.

Dimensions for annular cuff 82 may be selected based on the type of surgical procedure that is being performed and the type and condition of the biological tissue to which attachment ring 30 is to be anchored. In one embodiment, annular cuff 82 has an outer diameter from about 30 mm to about 50 mm, and an inner diameter from about 10 mm to 25 mm.

Figure 3A:
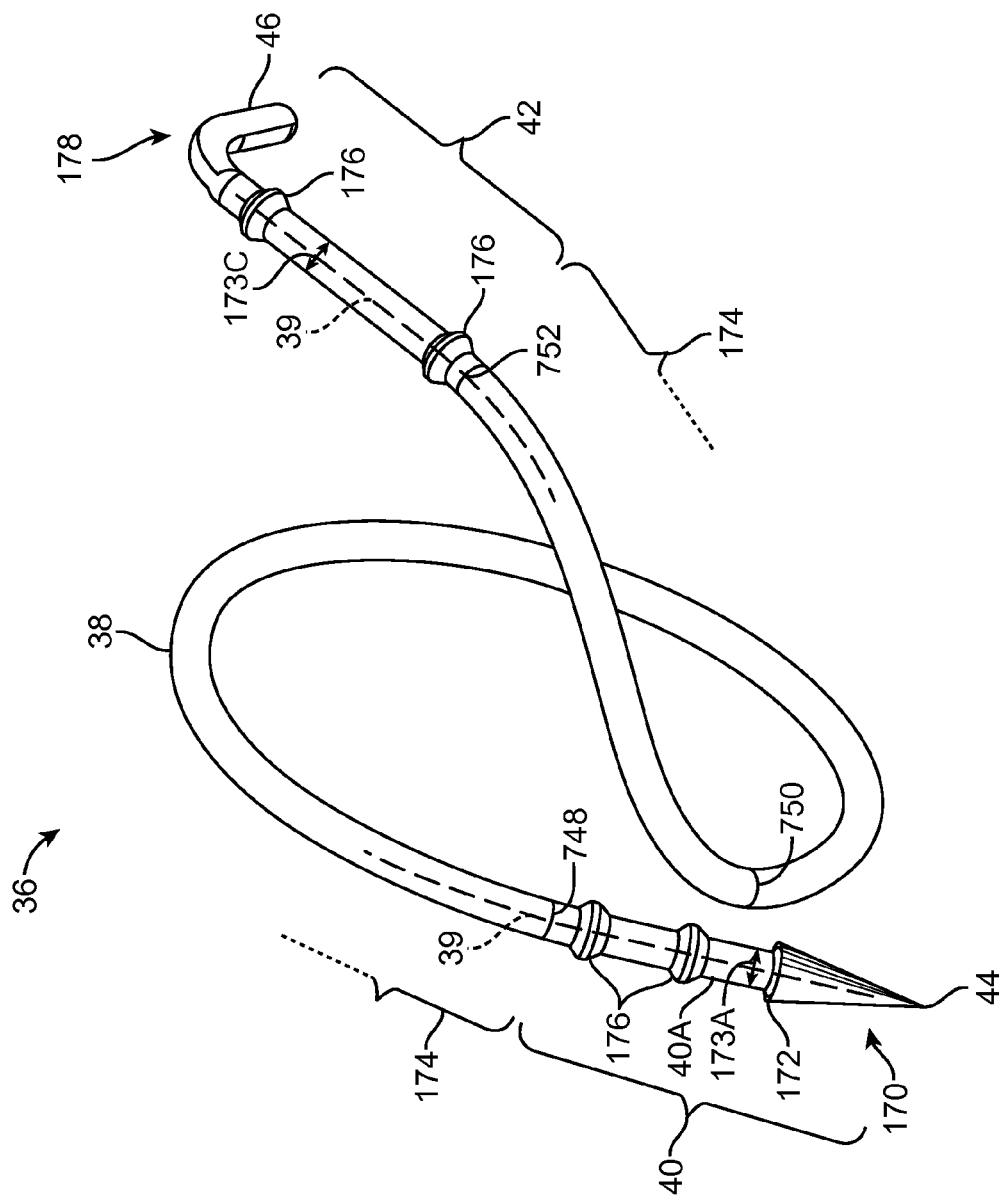
FIG. 3A-3D are perspective and other views of an exemplary securement clip to be loaded into and deployed out of an applicator tool.
Figure 3B:
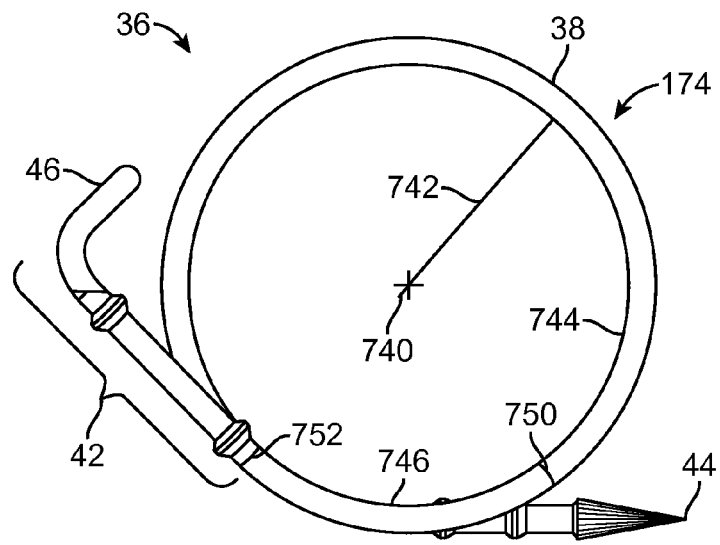
Figure 3C:
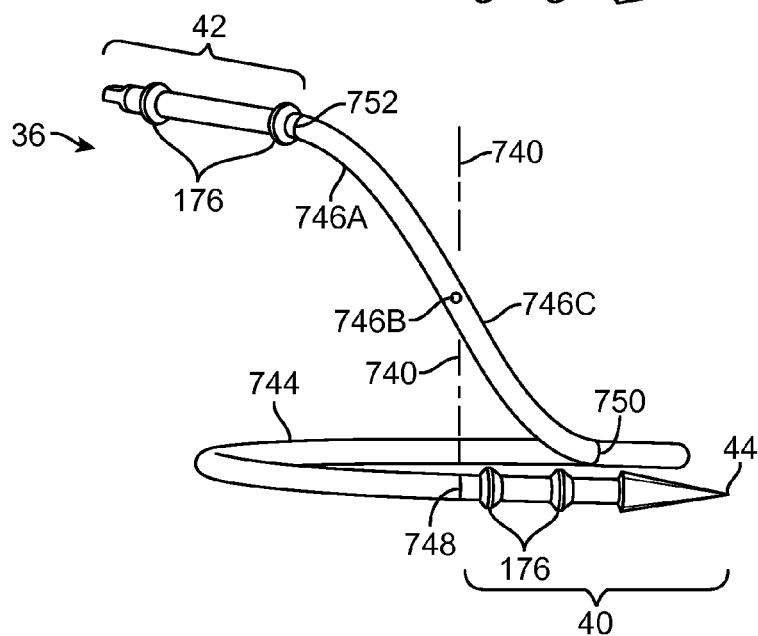
Figure 3D:
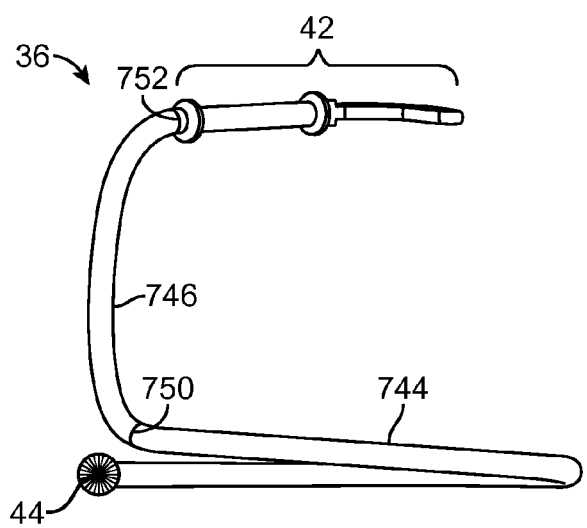

FIG. 3A shows exemplary clip 36 for anchoring attachment ring 30 to biological tissue. FIGS. 3B-3C show various views of clip 36 of FIG. 3A. In FIGS. 3A-3D, clip 36 is shown in its natural and unconstrained state prior to being loaded into applicator tool 10. Clip 36 can be made of titanium or other material suitable for implantation within a human or animal body or a mammalian body. In one embodiment, clip 36 is made of a nickel-titanium alloy (e.g. Nitinol), copper-zinc-aluminum alloy, or other material having shape memory and/or superelastic properties.

In use, clips 36 are contained within forward end 12 of applicator tool 10. Each clip 36 includes wire body 38 having forward segment 40 and rear segment 42. Forward segment 40 has sharp tip 44 for piercing a portion of attachment ring 30 and underlying biological tissue. Catch 46 protrudes out from rear segment 42 and is pushed forward during operation of applicator tool 10. Clips 36 are constrained in a straightened configuration within forward end 12 of applicator tool 10. In various embodiments, the clips are formed of shape memory material and make use of the shape memory properties. When deployed out of forward end 12, exemplary clips 36 will autonomously coil radially outward away from axial centerline 54 (FIG. 1E) in a direction away from forward end 12 due to elastic memory of wire body 38. In various embodiments, the clips have a generally straight shape in a stowed or undeployed condition and a relatively curved shape when deployed. In various embodiments, at least a portion of the clips extend outwardly away from the forward end without the use of external forces when they are unconstrained. One will appreciate that the shapes and configurations of the clips in the deployed and undeployed conditions may be modified depending on the application. For example, the clips may have a relatively straighter shape when deployed.

Referring to FIG. 1E, clips 36 are constrained within a plurality of clip holders 47 forming parts of clip tube 48. Clip tube 48 is a hollow, cylindrical sleeve. Each clip holder 47 comprises clip groove 52 formed within walls of clip tube 48. Clip groove 52 has axial slot opening 53 that faces radially outward, away from axial centerline 54 of clip tube 48. An end portion of catch 46 of each clip 36 extends out of axial slot opening 53 of clip groove 52. One exemplary catch 46 is shown for ease of illustration, and it will be understood there will be a catch protruding out of each clip groove 52 that contains clip 36. Clip pusher surface 51 abuts catch 46 from behind and is configured to push clips 36 out of forward opening 61 of clip groove 52.

Clip grooves 52 have sidewalls 57 that extend substantially parallel to axial centerline 54 and substantially non-perpendicular to outer surface 45 of clip tube 48. In other embodiments, sidewalls 57 are substantially perpendicular to outer surface 45.

Catch 46 of each clip 36 abuts sidewalls 57 of clip groove 52, which prevents clip 36 from twisting about its central axis 39 while contained inside clip groove 52. Catch 46 and sidewalls 57 help to ensure that the curved trajectory of tip 44 will be in the desired direction relative to attachment ring 30. The direction followed by tip 44 is controlled in part by the angle of sidewalls 57 and by the initial shape of clip 36 prior to being loaded in applicator tool 10. As shown in FIG. 1E, sidewalls 57 are at an oblique angle measured from radial line 54R. Radial line 54R is a radial line that extends out from the center of clip tube 48 and is perpendicular to axial centerline 54. The oblique angle, indicated by arrow B, can be from about 10 degrees to about 80 degrees, and more narrowly from about 30 degrees to about 60 degrees, and more narrowly at about 45 degrees. In some embodiments, the angle of sidewalls 57 causes clips 36 to deploy into biological tissue at the oblique angle relative to radial line 54R. A change in oblique angle B changes the distance between the center of applicator tool 10 and the point at which the clip tip 44 exits the biological tissue, and thus changes the size of the clip foot print. Oblique angle B is important since clip tip 44 should exit the biological tissue at a point slightly beyond the outer circumference of attachment ring 30. A larger oblique angle B results in a smaller clip footprint and thereby increases hemostasis and stabilization of attachment ring 30 to the biological tissue. The term "clip footprint" refers to the surface area of biological tissue encircled by a plurality of deployed clips.

In FIG. 1E, oblique angle B is the same for sidewalls 57 of all clip grooves 52. In other embodiments, clip grooves 52 can have varying oblique angles. For example, a first group of clip grooves 52 at a first area of clip tube 48 have sidewalls 57 oriented at oblique angle B that is different than that of a second group of clip grooves 52 at a second area of clip tube 48. For example, on the same clip tube, oblique angle B can be 30 degrees for some clip grooves 52, and 45 degrees for other clip grooves, and 60 degrees for other clip grooves 52.

Figure 1F:
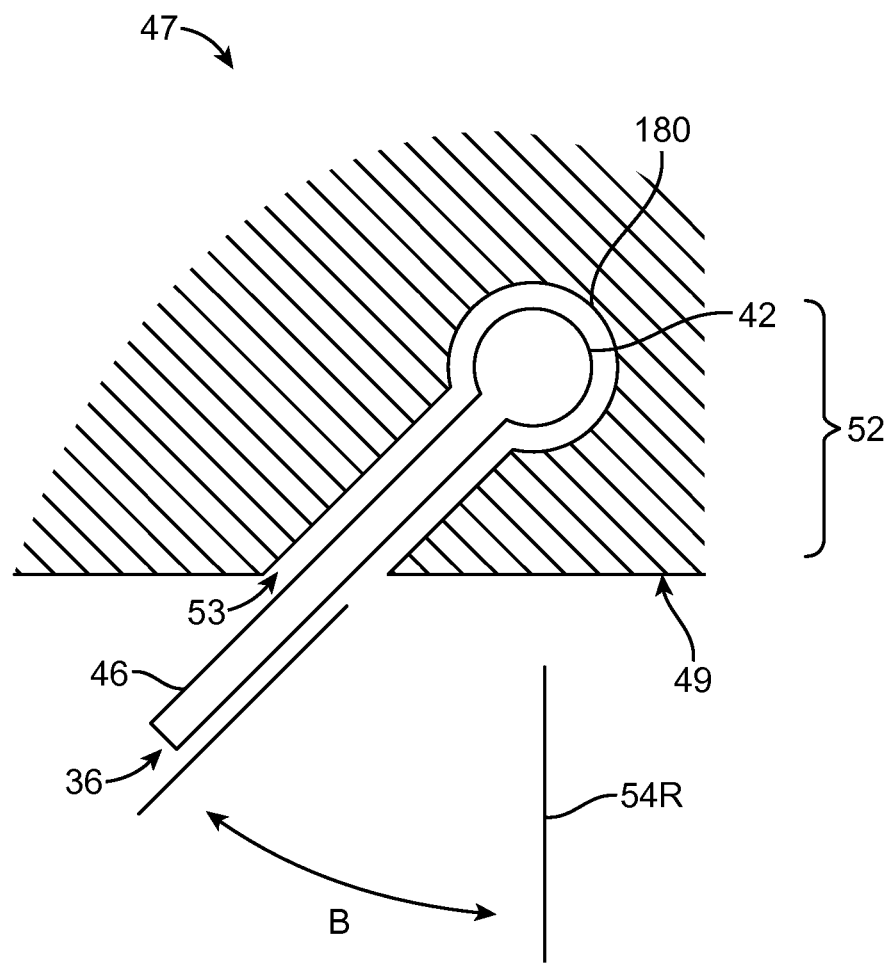
FIG. 1F is a partial cross-section view of an exemplary clip holder of the applicator tool of FIG. 1A.

FIG. 1F shows a cross-section view of clip holder 47. Clip groove 52 has bottom portion 180 that is shaped and sized to receive and contain clip 36. Bottom portion 180 is shaped and sized to receive and contain bumps 176 and barbed head 170 of clip 36. Axial slot opening 53 at the top of clip groove 52 is narrower than the space within bottom portion 180 in order to prevent forward segment 40, medial segment 174, and rear segment 42 of clip from passing through axial slot opening 53. The space or gap within axial slot opening 53 is less than the diameter of clip wire body 38. The relatively narrow space or gap within slot opening 53 prevents clip 36, while contained in applicator tool 10, from moving from a straight configuration to its natural curved configuration (shown in FIGS. 3A-3D). Catch 46 of clip 36 is sized to pass through axial slot opening 53, which allows catch 46 to be pushed by clip pusher surface 51 (FIG. 1E).

There are twelve clip holders 47 circumferentially arranged on clip tube 48 at substantially equal angular spacing of about 30 degrees apart from each other. In other embodiments, a fewer number or a greater number of clip holders 47 are arranged around the clip tube than what is shown in FIG. 1E. The number of clip holders and clips depends upon a variety of factors, such as the type of surgical procedure that is being performed and the type and condition of the biological tissue to which attachment ring 30 is to be anchored. In other embodiments, the clip holders are not arranged at equal angular spacing, such that the clip holders are closer to each other at one area of clip tube 48 as compared another area of the clip tube 48.

Cinching tube 58 is a hollow, cylindrical sleeve. Cinching tube 58 contains and is substantially coaxial with clip tube 48. Clip pusher surface 51 (FIG. 1E) is located at the forward end of cinching tube 58. Cinching pins 60 are attached to cinching tube 58 and protrude axially in front of clip pusher surface 51. Cinching tube 58 is controlled by clip deployment handle 18 (FIG. 1). Clamping tube 64 is a hollow, cylindrical sleeve. Clamping tube 64 contains and is substantially coaxial with clip tube 48 and cinching tube 58. Clamping tube 64 is controlled by handle 18.

A method for anchoring attachment ring 30 will now be described together with applicator tool 10, though it should be understood that other applicator tools may be used to perform the method. It is to be understood that, depending on the type of applicator tool used and depending on clinical need, some steps described below may be performed simultaneously as a single step, performed in a sequence other than described below, or may be omitted.

Exemplary steps for applicator tool stabilization are as follows. Referring to FIG. 1A, a user such as a medical practitioner grasps grip 16 to position main body 70 of attachment ring over biological tissue. Suction may be applied to tube fitting 25 which conveys the suction to suction cup 26 (FIG. 1E) at the front of applicator tool 10. Suction cup 26 engages the biological tissue and stabilizes applicator tool 10 against movement relative to the biological tissue. Steps for stabilization can be performed whenever needed, which can be before, during, and/or after any of the steps for clip deployment, clamping, and cinching described below.

As used herein, the phrase "clip deployment" refers to forward movement of clips 36 out of applicator tool 10, through attachment ring 30, and into biological tissue.

Exemplary steps for clip deployment are as follows. The user rotates handle 18 to begin deployment of clips 36 out of applicator tool 10. Handle rotation causes clamping tube 64 (FIG. 1A), cinching tube 58, and clamping ring 100 to slide axially forward onto clip tube 48 in the direction of arrow C. Forward end of cinching tube 58 has clip pusher surface 51 (FIG. 1E) that pushes clips 36 out of applicator tool 10, through cinching ring 86 and attachment ring main body 70, and into the biological tissue. As clip pusher surface 51 continues to push rear segment 42 of clips 36, sharp tips 44 of clips 36 follow a curved path into and then out of the biological tissue. At the conclusion of clip deployment, clips 36 are completely pushed out of applicator tool 10. Catch 46 of each clip 36 is located between the forward end of clip tube 48 and top surface 91 (FIG. 2D) of cinching ring 86. Sharp tip 44 of each clip 36 is located between clamping ring 100 and clamp surface 67 (FIGS. 1A and 2D) of attachment ring main body 70.

As used herein, the phrase "clamping" refers to moving clamping ring 100 (FIG. 1A) closer to attachment ring main body 70 in order to prevent sharp tips 44 of clips 36 from pulling backwards into the biological tissue.

Exemplary steps for clamping are as follows. After clip deployment, the user pulls clamp release 21 (FIG. 1A) downward, which allows clamping tube 64 to slide forward over cinching tube 58. The user rotates handle 18 to move clamping tube 64 and clamping ring 100 axially forward over cinching tube 58 and toward attachment ring main body 70.

As shown in FIG. 2D, clamping ring 100 includes flexible arms 700 with radially inward facing catch members 702. Each catch member 702 is in the form of a pawl that locks clamping ring 100 onto attachment ring main body 70. As clamping ring 100 is pushed onto main body 70, flexible arms 700 bend as leading face 702A of each catch member 702 slides over and is pushed radially outward by cylindrical wall 72 of attachment ring main body 70. Catch members 702 enter lock feature 704 in the form of groove formed into the outer surface of cylindrical wall 72. Rear face 702B of each catch member 702 engage lock feature 704 and prevents clamping ring 100 from sliding off attachment ring main body 70.

At the conclusion of clamping, clamping ring 100 covers clamp surface 67 of attachment ring main body 70. Ridges or teeth 706 are arranged around the outer perimeter of clamping ring 100 and are configured to trap at least a portion of clip forward segment 40 (FIG. 3A) between clamping ring 100 and attachment ring main body 70. Each groove or space 708 between teeth 706 is sized to allow passage of clip wire body 38 (FIG. 3A) and to prevent passage of barbed head base 172 and bumps 176 on clip forward segment 40.

After clip deployment and clamping, there may be some slack or excess length of clip 36 below the biological tissue due to curvature, thickness, and/or density of biological tissue or due to other factors. The slack or excess length of clip 36 can result in a gap between clip wire body 38 and the interior surface of the biological tissue.

As used herein, the word "cinching" refers to tightening of clips 36 against the biological tissue. The tightening of clips 36 may include a reduction of slack or excess length of clip 36 that may exist between clip wire body 38 and the interior surface of the biological tissue after clip deployment and clamping.

Exemplary steps for cinching are as follows. After completion of clip clamping, the user rotates handle 18 which causes cinching tube 58 to rotate relative to clip tube 48 and connector mechanism 28 (FIG. 1E). During rotation of cinching tube 58, cinching pins 60 (FIG. 1E) on cinching tube 58 engage cinching feature 89 (FIGS. 2A and 2D) on cinching ring 86, and forces cinching ring 86 to rotate relative to attachment ring main body 70. During rotation of cinching ring 86, top surface 91 (FIG. 2D) of cinching ring 86 engages catch 46 (FIG. 3A) of each of clips 36. As a result, rear segment 42 of clips 36 are pulled circumferentially within chamber 75 (FIG. 2D) enclosed between attachment ring main body 70 and cinching ring 86. Pulling of rear segment 42 of clips 36—while tips 44 of clips 36 are trapped between clamping ring 100 and clamp surface 67 (FIG. 2D) of main body 70—causes clips 36 to tighten against the biological tissue.

The above described rotation and pulling during cinching is generally in the circumferential direction of arrow D (FIG. 2D). However, it will be appreciated that rotation can be in the opposite circumferential direction for other embodiments.

Exemplary steps for separating attachment ring 30 from applicator tool 10 are as follows. The user discontinues any suction that may have been applied to suction cup 26 (FIG. 1E). The user pulls disengagement knob 24 which controls movable lock elements 29 of attachment mechanism 26. The pulling allows lock elements 29 to move and disengage internal annular groove 77 of attachment ring main body 70. Next, the user pulls applicator tool 10 away from attachment ring main body 70, while main body 70 remains secured by clips 36 to the biological tissue, and while clamping ring 100 and cinching ring 86 remain locked onto main body 70.

Further details of applicator tool 10 are as follows. FIG. 1B shows clamping tube 64 removed to expose L-shaped guide slot 718 formed in cinching tube 58. FIG. 1C shows clamping tube 64 and cinching tube 58 removed to expose stationary tube 720 which is fixed to clip tube 48 and grip 16. L-shaped guide slot 722 is formed in stationary tube 720. FIG. 1D shows stationary tube 720 removed to expose drive member 724, in the shape of a worm gear or Archimedes screw, which is fixed to deployment handle 18. Helical slot 726 is formed in drive member 724 and receives drive pin 730 (FIGS. 1A and 1B) coupled to clamping tube 64 and cinching tube 58. When the user rotates handle 18, helical slot 726 pushes drive pin 730 through guide slots 718 and 722, which are sized and shaped to cause clamping tube 64 and cinching tube 58 to move as described above for clip deployment, clamping, and cinching.

Further details of attachment ring 30 are as follows. Cinching ring 86 (FIGS. 2A and 2D) is contained within interior space 73 of cylindrical wall 72 of main body 70. Central through-hole 88 of cinching ring 86 is substantially centered upon axial centerline 78 of main body 70. Peripheral through-holes 90 are formed through axial top surface 91 of cinching ring 86 and have a diameter sized to receive clips 36 (FIG. 3A) contained within forward segment 12 of applicator tool 10. The passageway of the through-holes 90 intersects annular cuff 82. Cinching feature 89 extends axially upward from top surface 91 of cinching ring 86. During the cinching process described above, cinching feature 89 engage cinching pins 60 (FIG. 1E) at the forward portion of cinching tube 58 of applicator tool 10. As shown in FIG. 2D, ratchet catch 96, in the form of a flexible arm, extends circumferential around and protrudes out from radially outward facing surface 94 of cinching ring 86. At the free end of each ratchet catch 96 there is pawl 97 that protrudes axially downward and is configured to engage ratchet members 76 of attachment ring main body 70. In use, cinching ring 86 is capable of rotating within main body 70 in only one direction. During such rotation, ratchet catch 96 bends as the ramped shape of leading edge 97A of pawl 97 slides over and is pushed upward by ratchet member 76 of main body 70. In the reverse direction, rear edge 97B pawl 97 engages ratchet member 76 of main body 70 and prevents rotation of cinching ring 86 in the reverse direction.

As shown in FIGS. 2A and 2D, attachment ring main body 70 includes interior cylindrical wall 732. Internal annular groove 77 is formed into interior cylindrical wall 732 for engagement with attachment device 28 of applicator tool 10 and for subsequent engagement with a cannula. The cannula can be as described in FIGS. 34 and 35 or any of the VAD inflow conduits described in U.S. Application Publication No. 2011/0118766 A1, which is incorporated herein for all purposes by reference.

Interior cylindrical wall 732 has annular lip 734 configured to retain cinching ring 86 within main body 70. Annular lip 734 forms one side of a retention groove and includes four recesses 736, each recess sized to receive one of four tabs 738 of cinching ring 86. Two tabs 738 are visible in FIG. 2D. The angular spacing between tabs 738 is the same as the angular spacing between recesses 736. When tabs 738 and recesses 736 are aligned, tabs 738 can pass axially through recesses 736. After tabs 738 are received into recesses 736, rotation of cinching ring 86 causes tabs 738 to slide within the retention groove and move out of alignment relative to recesses 736. Thereafter, annular lip 734 prevents cinching ring 86 from pulling apart from attachment ring main body 70. The angular spacing between tabs 738 is such that with continued rotation of cinching ring 86, only one tab 736 comes into alignment with any of recesses 736. A complete 360-degree rotation is needed to allow realignment of all the tabs 738 and recesses 736 and to allow removal of cinching ring 86 from main body 70.

Further details of clip 36 are as follows. As shown in FIGS. 3A-3D, clip 36 has a non-uniform thickness. Central axis 39 extends axially through the center of wire body 38 which extends from sharp tip 44 to catch 46. Wire body 38 forms a spiral or helix. Sharp tip 44 forms the point of barbed head 170. Barbed head 170 flares radially outward from central axis 39 so that barb head 170 widens from tip 44 to base 172. Base 172 is attached to and abuts thinner portion 40A of forward end 40. Base 172 is wider or thicker than thinner portion 40A. Thinner portion 40A of forward end 40 has thickness 173A that is perpendicular to central axis 39 and is less than the thickness of base 172. Base 172 can be shaped and sized to engage teeth 706 of clamping ring 100, which inhibits or prevents tip 44 from pulling out of attachment ring 30 after clip deployment and clamping.

Forward end 40 of clip 36 is substantially straight so that tip 44 moves in a substantially straight path for an initial period of time after the start of clip deployment out of applicator tool 10. The axial length of forward end 40 is selected to control the depth of clip penetration into the biological tissue. As clip deployment continues, tip 44 moves in a substantially curved direction due to the natural curvature of medial segment 174 of wire body 38.

Wire body 38 includes a series of bumps 176 that protrude radially outward from central axis 39. Although four bumps 176 are illustrated, a lesser or greater number of bumps 176 can be implemented. These bumps are designed for purpose of securing the wire body by engaging with a corresponding mating part. Thus, as an alternative or in combination with bumps 176, other securing features such as a void or depression into clip wire body can also be used for purpose of securement. In forward segment 40, bumps 176 may engage teeth 706 of clamping ring 100. In rear segment 42, bumps 176 may engage cinching ring 86 during the cinching process, and may accommodate variations in the thickness of biological tissue. In other embodiments, bumps 176 can be located on medial segment 174.

As shown in FIG. 3A, rear segment 42 includes L-bend portion 178 that is narrower or thinner than other parts of rear segment 42. Catch 46 forms the free end of L-bend portion 178. Other parts of rear segment 42 have thickness 173C which is perpendicular to central axis 39 and is greater than the thickness of L-bend portion 178 and catch 46. L-bend portion 178 and catch 36 can be formed by stamping, coining, or flattening the free end of rear segment 42 so that L-bend portion 178 and catch 46 are narrower or thinner than other parts of clip 36. The reduced thickness of catch 46 allows it to pass through axial slot 53 (FIG. 1E) of clip tube 48. Other parts of wire body 38 have thicknesses that are too large to pass through axial slot 53.

FIG. 3B shows a view of clip 36 along axis 740 substantially perpendicular to radius of curvature 742 of medial segment 174. Radius of curvature 742 and/or length of medial segment 174 are selected to ensure that tip 44 moves to a position between clamping ring 100 and camp surface 67 of attachment ring main body 70 during clip deployment. As viewed along axis 740, medial segment 174 forms a complete 360-degree loop.

As shown in FIG. 3C, medial segment 174 includes a coil portion 744 and s-curve portion 746. Coil portion 744 connects to forward segment 40 at line 748 and connects to s-curve portion 746 at line 750. S-curve portion 746 is s-shaped in the sense that it includes concave downward part 746A, concave upward part 746C, and inflection point 746B between parts 746A and 746C. S-curve portion 746 connects to rear segment 42 at line 752. S-curve portion 746 is shaped and oriented to reduce the circumferential pulling force needed during cinching. The helix formed by the entire wire body 38 is in the same direction as cinching. Also, the helix formed by the entire wire body 38, at its natural state shown in FIGS. 3A-3D before being loaded into applicator tool 10, simulates the shape of clip 36 after clip deployment, clamping, and cinching.

In some embodiments, the diameter of wire body 38 can range approximately from about 0.010 inch to about 0.025 inch. The diameter of wire body 38 corresponds to thickness 173A and 173C described above. The diameter of bumps 176 can range approximately from about 0.030 inch to about 0.040 inch. The height of bumps 176 ranges approximately from about 0.005 inch to about 0.010 inch from base to peak. The depth of depressions into clip wire body ranges approximately from about 0.005 inch to about 0.010 inch from base to valley. The bump height or depression depth corresponds to the radial distance from the bump peak to bump base or from the diameter of the wire body to the valley of the depression. The overall length of clip 36 from tip 44 to L-bend portion 178 ranges approximately from about 0.75 inch to about 2 inch. Deployment angle (oblique angle B described above) can vary from 0 degree up to 90 degrees.

In some embodiments, the clip may have no bumps 176.

In some embodiments, the clip may have no s-curve portion 746.

Figure 4:
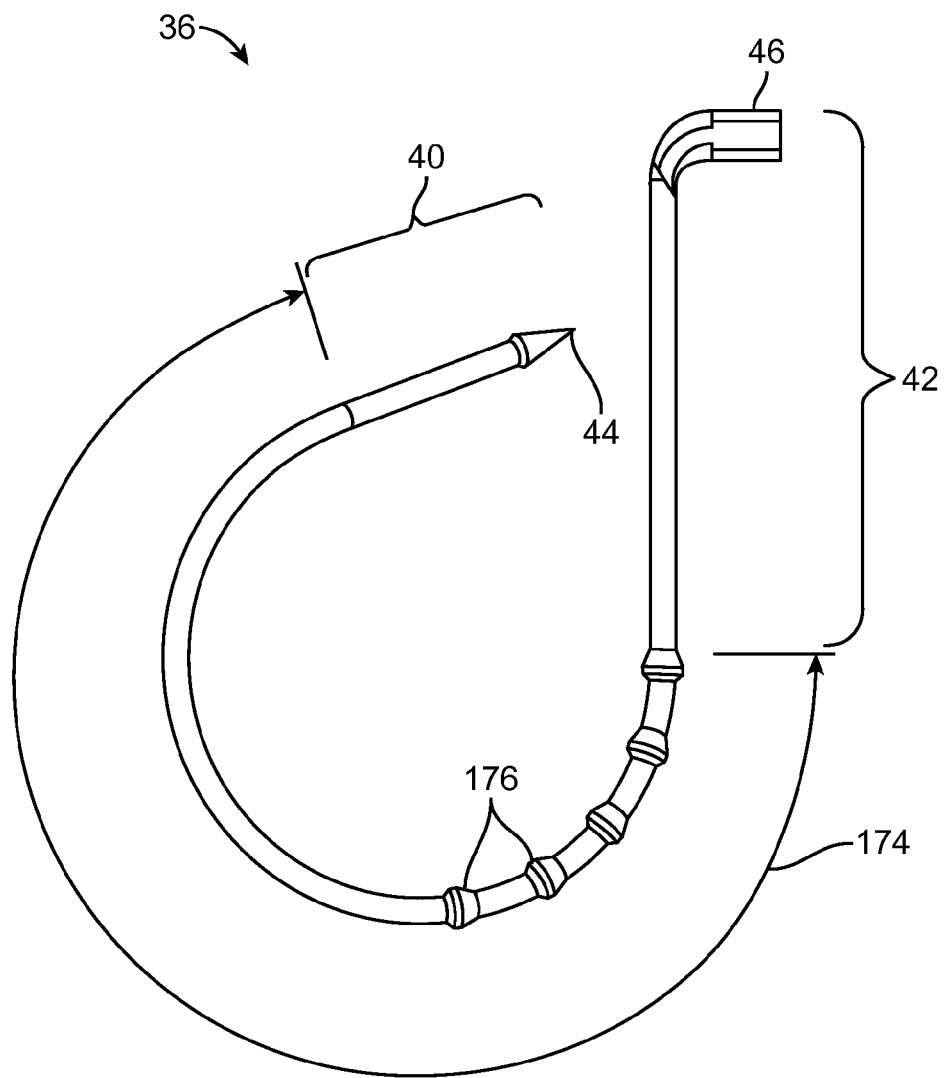
FIG. 4 is a side view of another exemplary securement clip similar to that of FIGS. 3A-3D.

In some embodiments, the clip has an alternative configuration shown in FIG. 4. Medial segment 174 forms a loop of less than 360 degrees.

In some embodiment, the clips contained within and deployed out of applicator tool 10 do not have the same length and shape. For example, some clips in one area of clip tube 48 may be longer and/or have a different curvature than other clips in another area of clip tube 48.

Figure 5:
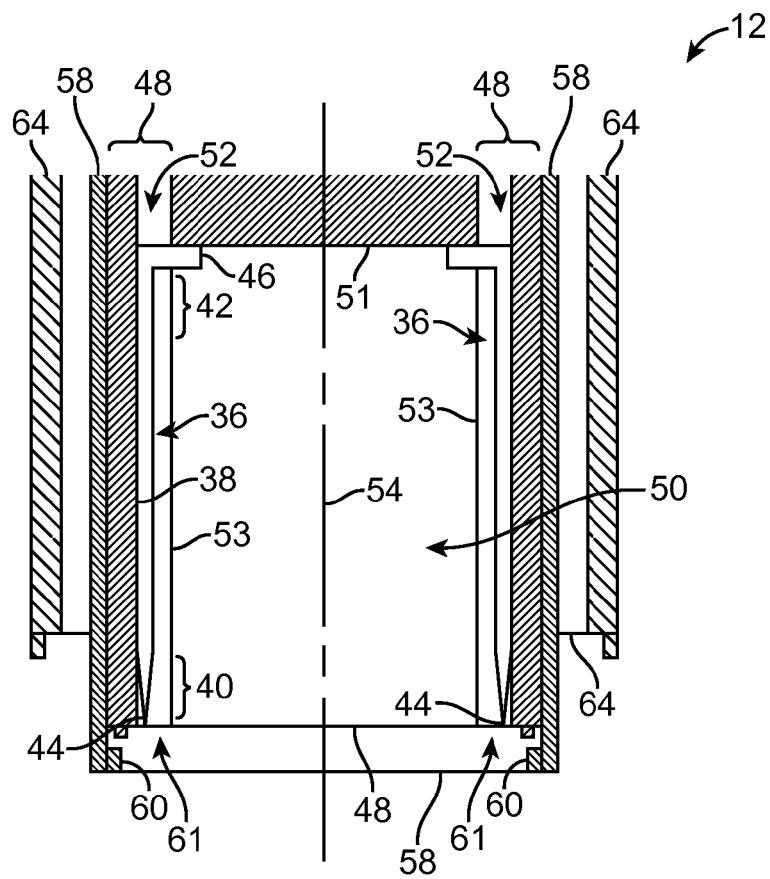
FIG. 5 is a cross-section view of an exemplary applicator tool forward end.
Figure 6:
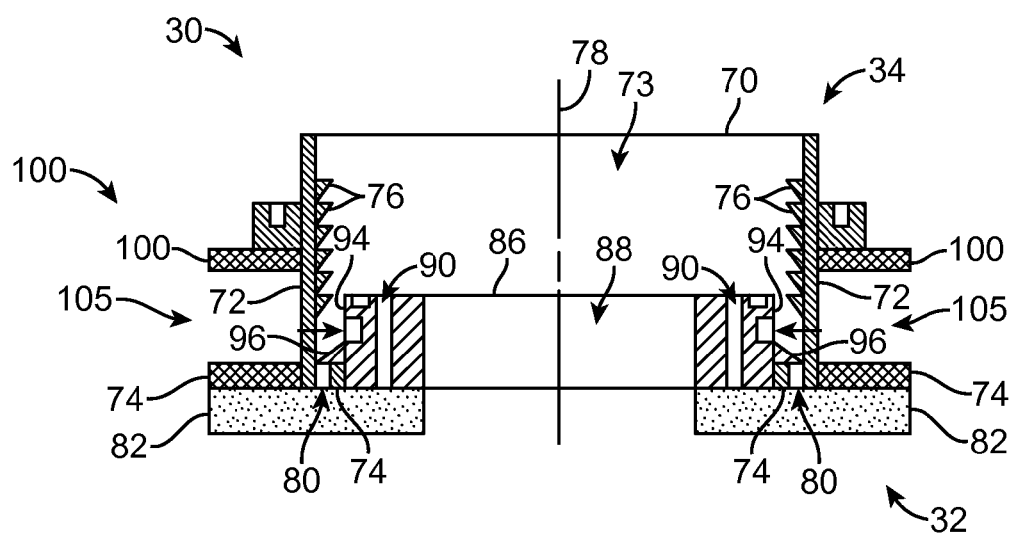
FIG. 6 is a cross-section view of another exemplary attachment ring similar to that of FIGS. 2A-2D.
Figure 7:
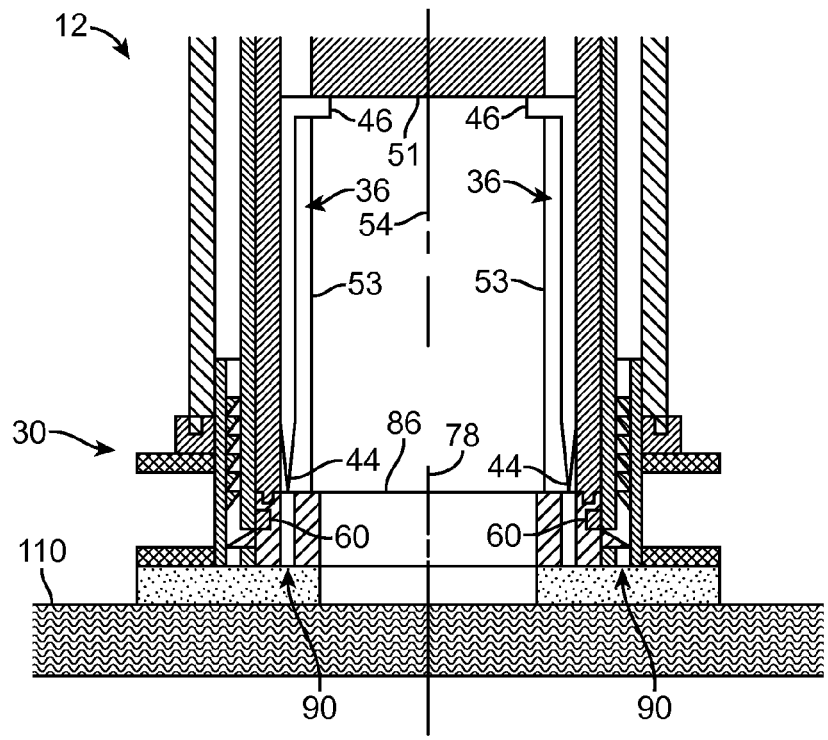
FIG. 7 is a cross-section view of the attachment ring of FIG. 6 mounted on the forward segment of FIG. 5 to form a coupling system, the view showing the front segment of the coupling system in an initial, undeployed condition on top of biological tissue.

FIGS. 5 and 6 show an applicator tool and an attachment ring according to other embodiments. Applicator tool forward end 12 is configured such that clip tube 48 is disposed within cinching tube 58, and cinching tube 58 is disposed within clamping tube 64. Clip grooves 52 are formed into an interior surface of clip tube 48 such that clip catch 46 points radially inward toward central axis 54. Clip pusher surface 51 is disposed within clip tube 48. As shown in FIG. 6, attachment ring 30 includes main body 70, clamping ring 100, and cinching ring 86. FIG. 7 shows applicator tool forward end 12 engaged to attachment ring 30 at the start of clip deployment. Attachment ring 30 is disposed over biological tissue 110. Biological tissue 110 can be any hollow organ or other anatomical structure to which a conduit, graft, cannula, or similar structure is to be coupled. For example, when preparing the heart for attachment with a VAD, biological tissue 110 can be myocardium at the ventricular apex of the heart.

Figure 8:
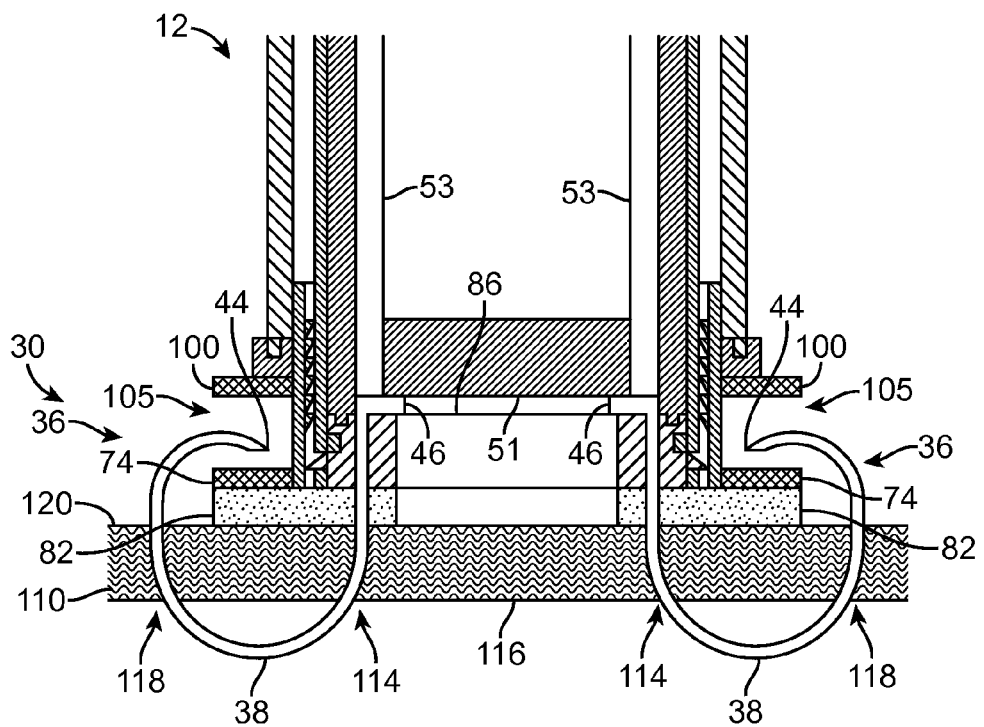
FIG. 8 is a cross-section view of the coupling system after FIG. 7, showing the coupling system in a deployed condition.

FIG. 8 shows the result of forward axial movement of clip pusher surface 51 at the conclusion of clip deployment. Tip 44 of clip 36 is disposed between clamping ring 100 and base 74 of attachment ring main body 70. While clip pusher surface 51 pushes catch 46 of clip 36, tip 44 pierces and enters biological tissue 110, wire body 38 of clip 36 bends outward away from the center of attachment ring 30. The bending occurs due to a natural tendency of wire body 38 to return to its original shape prior to being loaded in a straight configuration within the applicator tool. In various embodiments, the clip is constrained in the straight configuration by the inner walls of the applicator tool in which it is loaded. Tip 44 follows a curved path. In various embodiments, the curved path has a generally uniform radius of curvature along its length. In various embodiments, the curved path has a compound or complex curvature. In various embodiments, the tip is pre-disposed to move to a curved shape configured to promote insertion through the attachment ring and/or biological tissue. Tip 44 passes out from a first point 114 on interior surface 116 of biological tissue 110, and reenters at a second point 118 on interior surface 116 at a distance away from first point 114. Tip 44 continues up and out of top surface 120 of biological tissue 110 and enters clamp gap 105 between base 74 and clamping ring 100.

Figure 9:
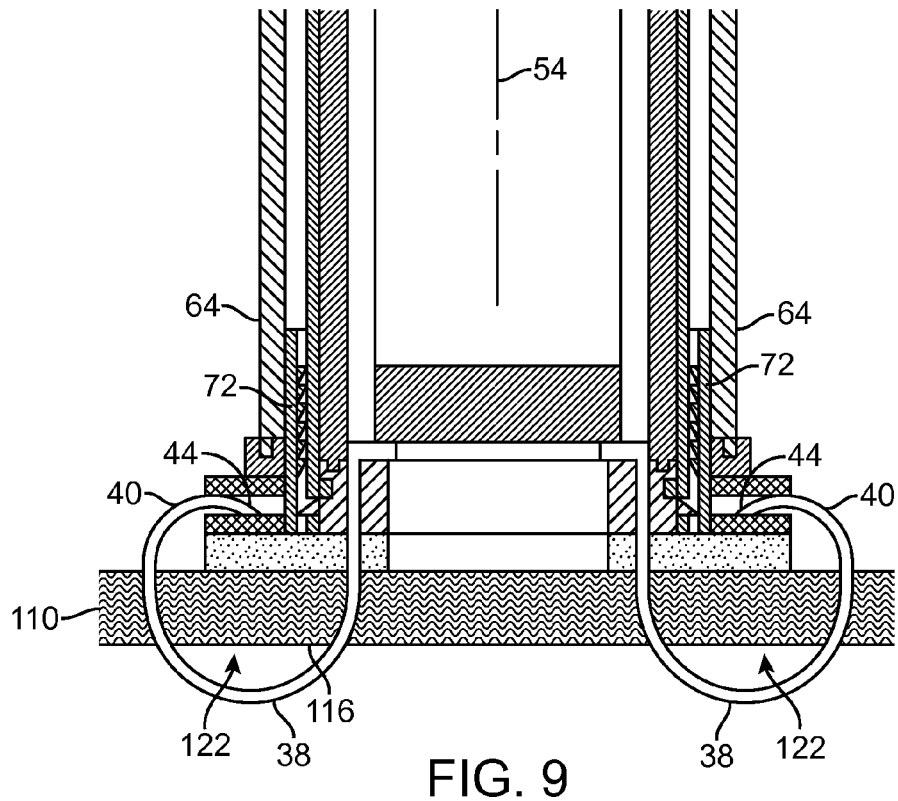
FIG. 9 is a cross-section view of the coupling system after FIG. 8, showing the coupling system in a clamped condition.

FIG. 9 shows the result of forward axial movement of clamping tube 64 at the conclusion of clip clamping. Tip 44 of clip 36 is trapped between clamping ring 100 and base 74 of attachment ring main body 70. Forward segment 40 of clips 36 are prevented from pulling back into biological tissue 110.

Due to curvature, thickness, and/or density of biological tissue 110 or due to other factors, there may be some slack or excess length of clip 36 below biological tissue 110. The slack or excess length of clip 36 is evident, for example, by gap 122 between wire body 38 and interior surface 116 of biological tissue 110.

Figure 10:
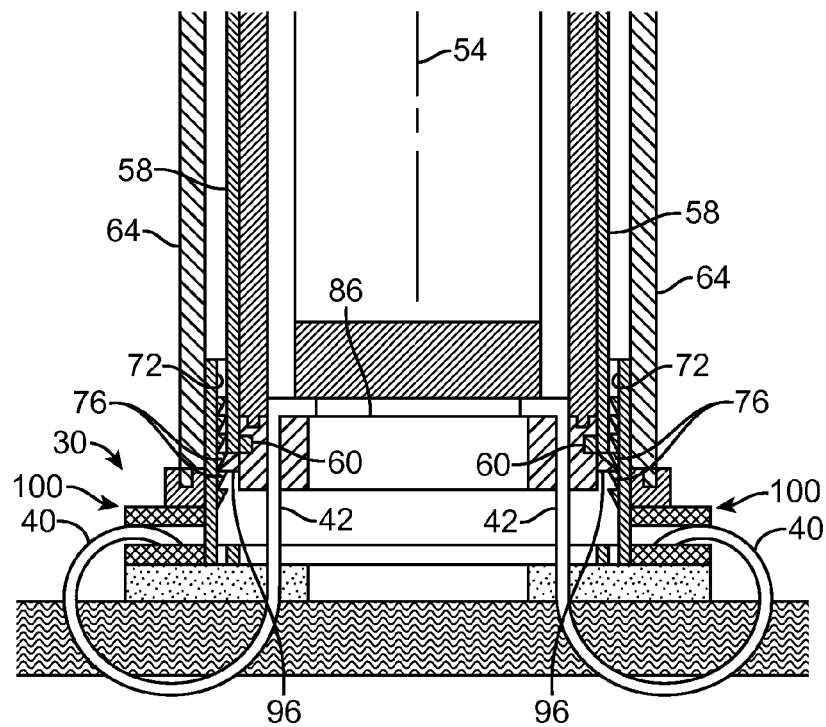
FIG. 10 is a cross-section view of the coupling system after FIG. 9, showing the coupling system in a cinched condition.

FIG. 10 shows the result of rearward axial movement of cinching tube 58 at the conclusion of cinching. The slack is taken out by cinching clips 36 against interior surface 116 of biological tissue 110. Cinching ring 86 has been moved axially relative to attachment ring main body 70 and further separated from base 74 of main body 70. Cinching ring 86 is locked in position by ratchet members 76 which hold ratchet catch 96 on cinching ring 86. As cinching ring 86 moves upward, ratchet catch 96 engages ratchet members 76 on cylindrical wall 72. After cinching, applicator tool forward end 12 is detached from attachment ring 30.

Figure 11:
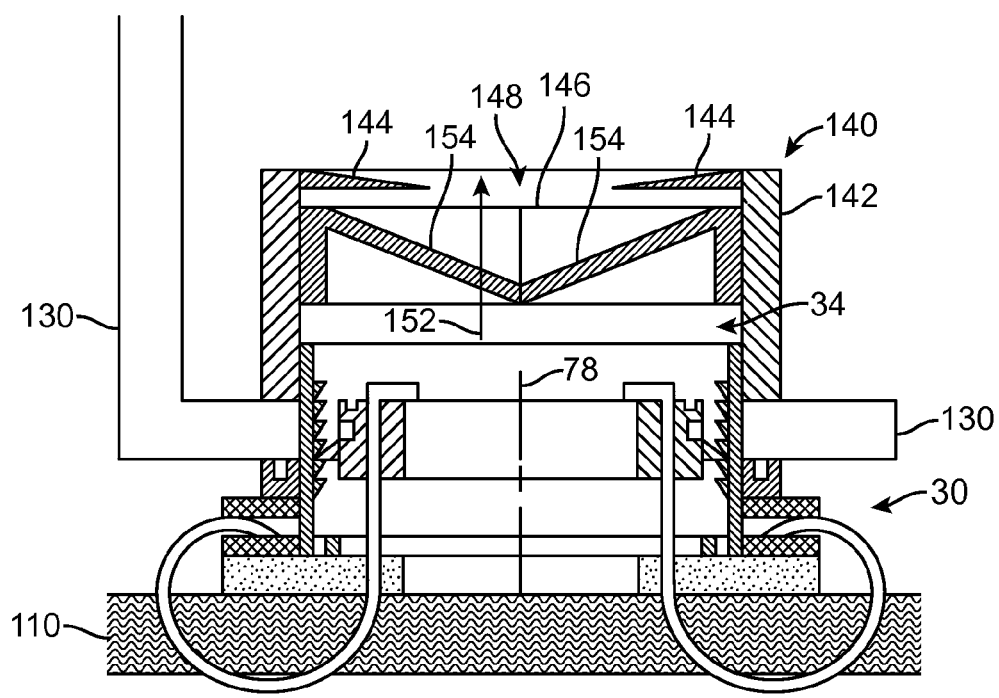
FIG. 11 is a cross-section view of the attachment ring after FIG. 10, showing the applicator tool removed and a clamp and valvular structure attached to the attachment ring.

As shown in FIG. 11, after removing applicator tool forward end 12, clamp 130 can be secured onto attachment ring 30 to stabilize the position of attachment ring 30 and underlying biological tissue 110. Valvular structure 140 is attached to top end 34 of attachment ring 30 so that there is a substantially liquid-tight seal between valvular structure 140 and attachment ring 30. The liquid-tight seal can be accomplished with a press-fit, a resilient gasket, helical screw threads, interlocking/mating features, mechanical fasters or a combination thereof on either one or both of valvular structure 140 and top end 34 of attachment ring 30.

Installation of valvular structure 140 allows an incision to be made in biological tissue 110 through attachment ring 30 without extensive loss of body fluid from the incision. For example, when preparing the heart for attachment with a VAD, valvular structure 140 prevents significant loss of blood and thus allows an incision to be made in the ventricular apex of the heart while the heart is beating and without the use of a heart-lung bypass machine. Depending on the type of surgical procedure and anatomical structure on which attachment ring 30 is anchored, it may not be desired or necessary to place valvular structure 140 on attachment ring 30. For example, placement of valvular structure 140 need not be placed on attachment ring 30 when preparing the heart for attachment with a VAD while the patient is connected to a heart-lung bypass machine.

Figure 12:
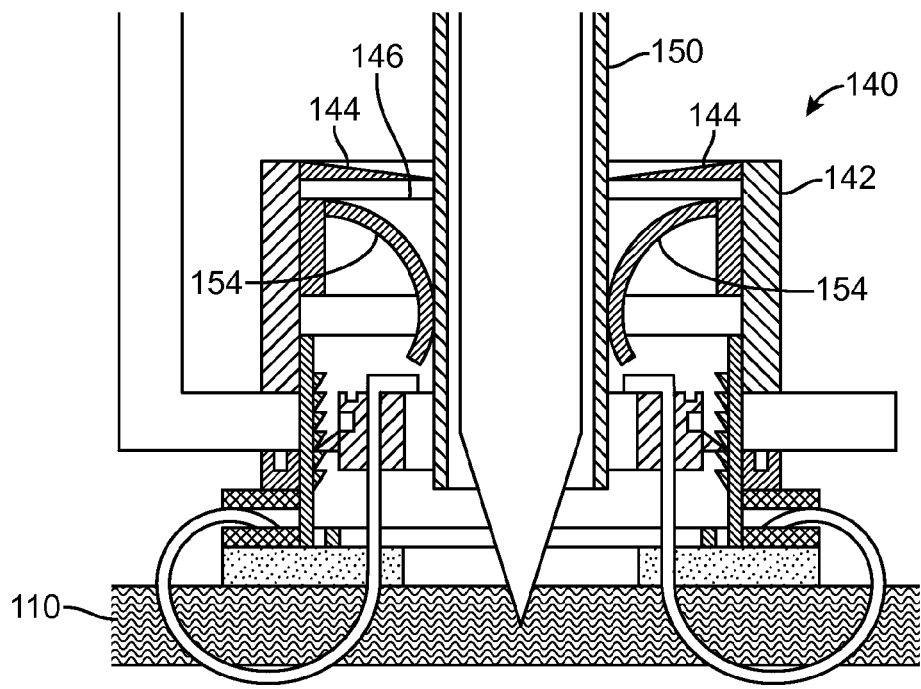
FIG. 12 is a cross-section view of the attachment ring and valvular structure after FIG. 11, showing an exemplary instrument inserted through the attachment ring and valvular structure.
Figure 13:
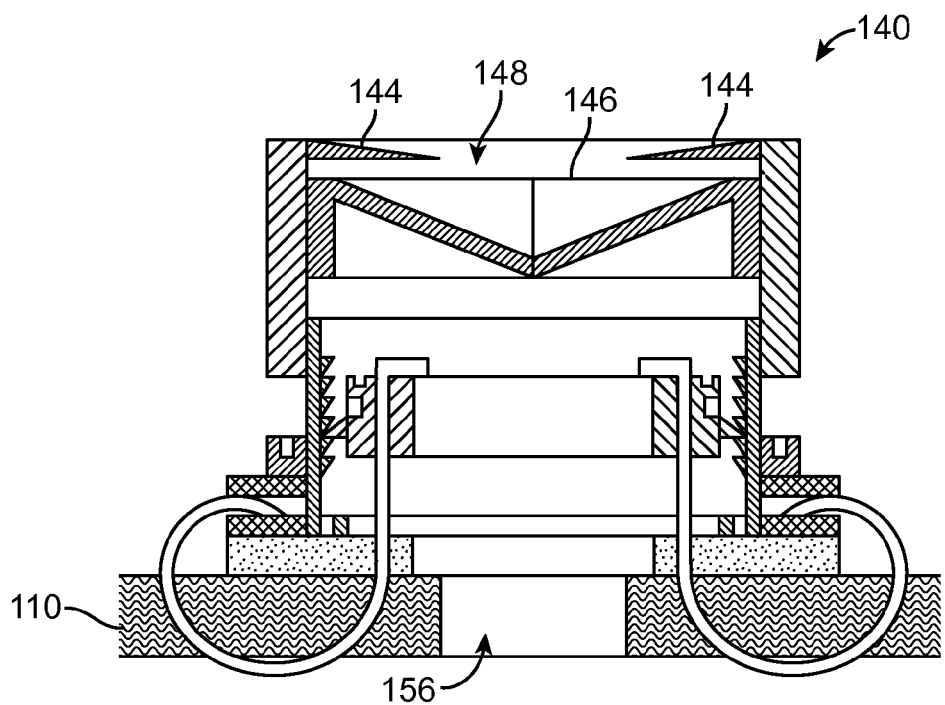
FIG. 13 is a cross-section view of the attachment ring and valvular structure after FIG. 12, showing a through-hole cut into the biological tissue by the instrument.

Referring to FIGS. 11-13, valvular structure 140 includes a housing 142, seal 144, and valve 146. Seal 144 and valve 146 are elastic and are configured to bend in response to passage of instrument 150 through them and to autonomously return to their original shape after instrument 150 is withdrawn. Seal 144 and valve 146 can be made of silicone rubber, polyurethane or other blood compatible polymers with elastic resiliency known in the art. Instrument 150 can be a slitting tool in one instance and a coring knife in a later instance. Suitable slitting tools and coring knives for use with attachment ring 30 and valvular structure 140 include without limitation the slitting tools and coring knives described in U.S. Application Publication No. 2011/0118766 A1, which is incorporated herein for all purposes by reference.

Annular seal 144 is attached to housing 142 and has a circular seal opening 148 substantially centered upon axial centerline 78 of attachment ring 30. Seal opening 148 is sized smaller than the outer diameter of instrument 150. As instrument 150 is passed through seal opening 148, a substantially liquid-tight seal is formed between the exterior surface of instrument 150 and annular seal 144, which prevents flow of body fluid therebetween.

Valve 146 is attached to housing 142 and is movable to and from a closed configuration (FIGS. 9 and 11) and an open configuration (FIG. 10). In the closed configuration, valve 146 provides a liquid-tight seal and substantially prevents flow of body fluid past valve 146 in the distal direction indicated by arrow 152. Valve 146 is a quadcuspid (i.e., four-leaflet) valve similar in configuration and function to quadcuspid valves described in U.S. Application Publication No. 2011/0118766 A1, which is incorporated herein for all purposes by reference. Valve 146 includes flexible members 154 configured to flex open in response to insertion instrument 150 and to close autonomously (FIG. 11), due to elastic resiliency of flexible members 154, upon removal of instrument 150.

In other embodiments, the valve of valvular structure 140 can be a tricuspid valve (similar to U.S. Application Publication No. 2011/0118766 A1, FIG. 14*a*), a bicuspid valve (similar to FIG. 15*a* of U.S. U.S. Application Publication No. 2011/0118766 A1), a dome valve, a diaphragm valve (similar to U.S. U.S. Application Publication No. 2011/0118766 A1, FIG. 15*f*), and combinations thereof, the entire contents of which publications are incorporated herein for all purposes by reference.

As shown in FIG. 13, instrument 150 has made a circular through-hole 156 in biological tissue 110. Any body liquid beneath biological tissue 110 is substantially prevented by valve 146 from flowing out of valvular structure 140.

Figure 14:
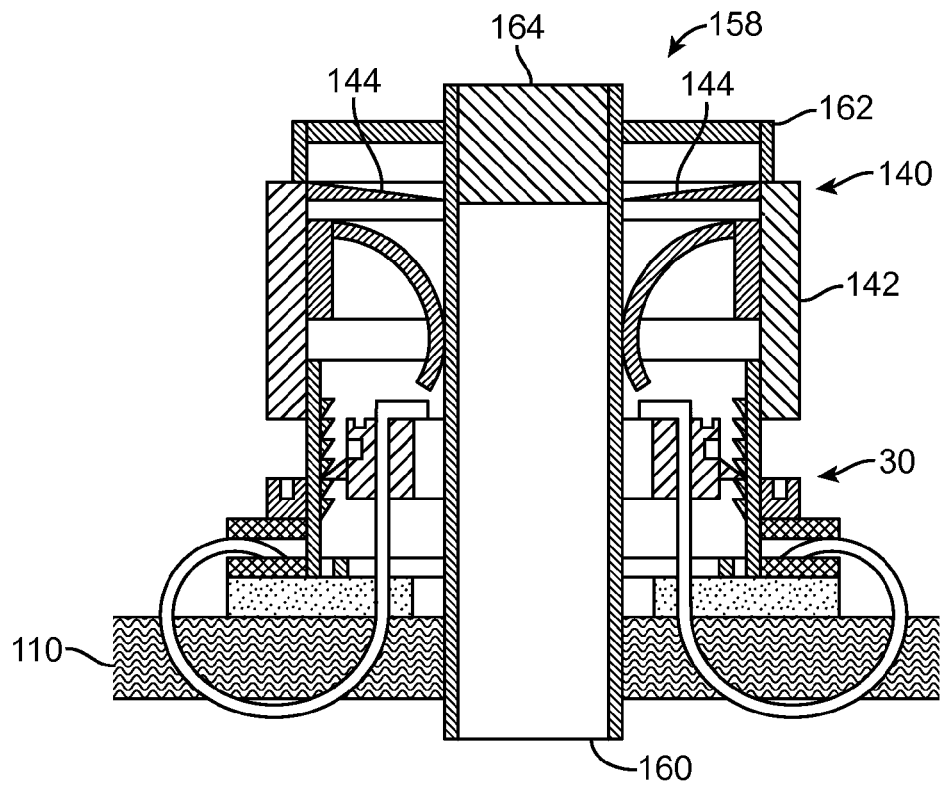
FIG. 14 is a cross-section view of the attachment ring and valvular structure after FIG. 13, showing an exemplary cannula inserted into the attachment ring, valvular structure, and through-hole in the biological tissue.
Figure 15:
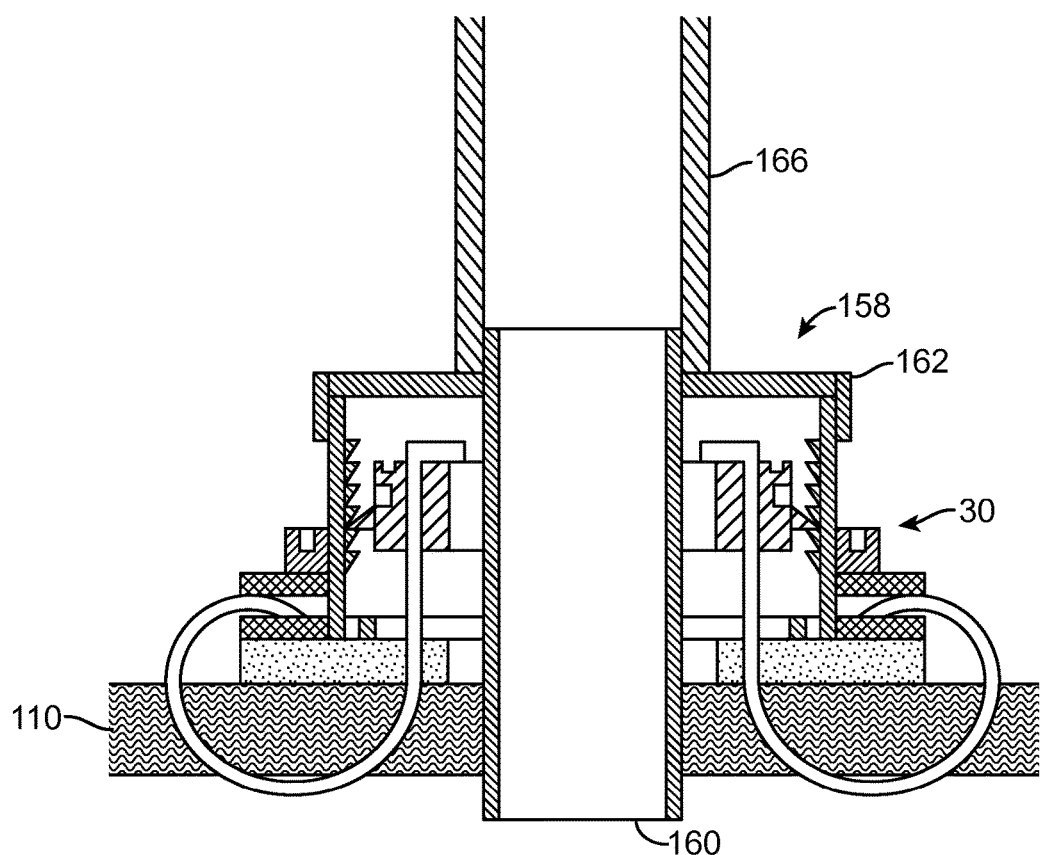
FIG. 15 is a cross-section view of the attachment ring after FIG. 14, showing the valvular structure removed and a fluid conduit connected to the cannula.
Figure 16:
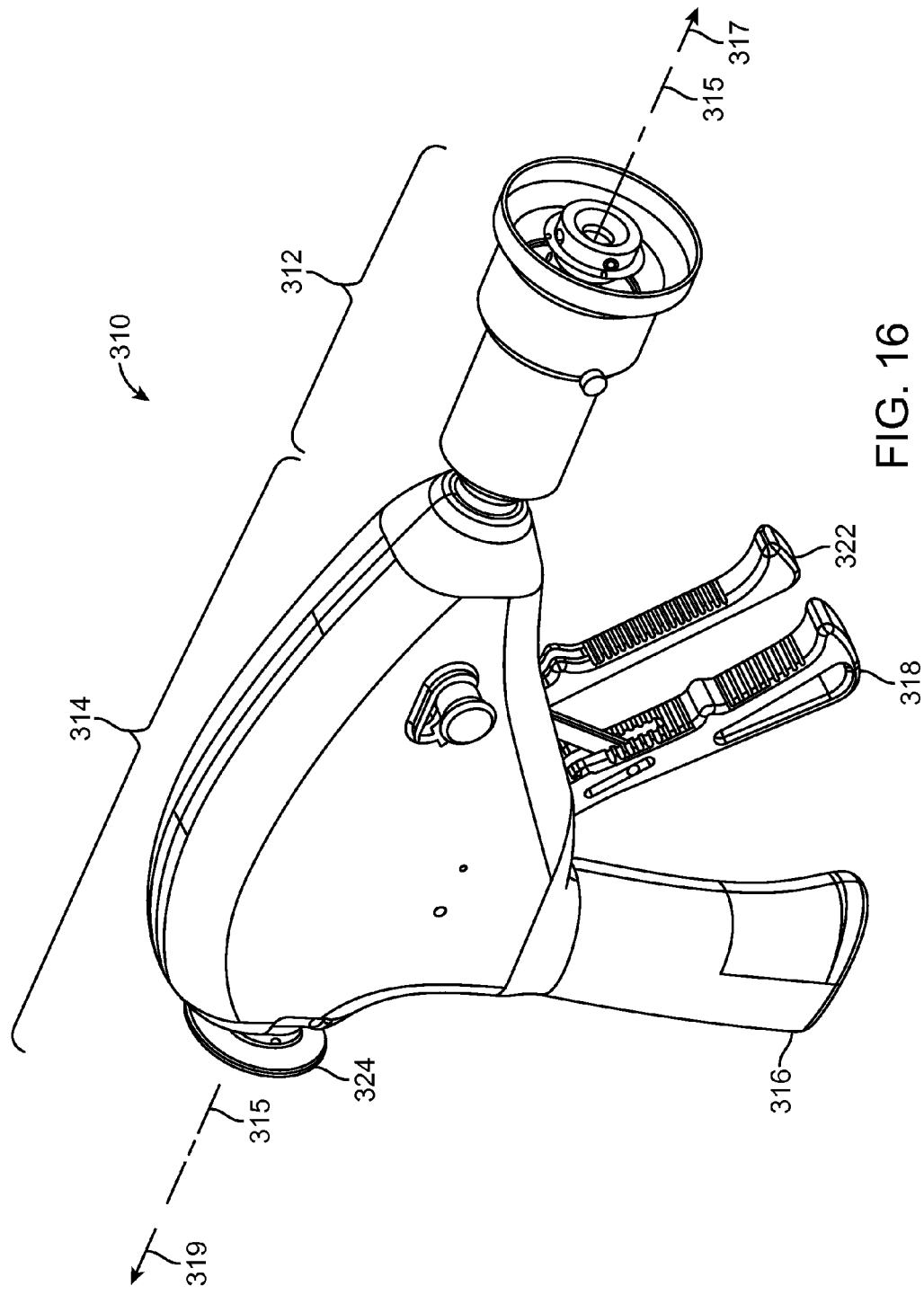
FIGS. 16-18 are perspective, perspective cutaway, and detailed cutaway views of an applicator tool similar to that of FIG. 1.

Referring to FIG. 14, cannula 158, or other tubular structure, can be inserted through valvular structure 140, attachment ring 30, and through-hole 156 in biological tissue 110. Cannula 158 is a type of prosthesis suitable for implantation within a human or animal body. Cannula 158 includes tube body 160, securement member 162 on tube body 160, and a removable plug 164 within tube body 160. As tube body 160 is passed through seal opening 148 (FIG. 11), a substantially liquid-tight seal is formed between the exterior surface of tube body 160 and annular seal 144, which prevents flow of body fluid therebetween. Plug 164 temporarily prevents any body liquid from escaping. When preparing a patient's heart for attachment with a VAD, cannula 158 can be any of the VAD inflow conduits described in U.S. Application Publication No. 2011/0118766 A1, which is incorporated herein for all purposes by reference. Plug 164 need not be present when escape of body fluid is not a concern, such as when the patient is connected to a heart-lung bypass machine during preparation for attachment with a VAD.

Referring to FIG. 13, after installation of cannula 158, valvular structure 140 can be removed from attachment ring 30 by dismantling or opening housing 142 of valvular structure 140. Valvular structure 140 includes a housing first portion and a housing second portion that are configured to be selectively locked together and moved apart from each other. The first housing portion is connected to the second housing portion by a slide member that locks the housing first portion and the housing second portion together. Valvular structure 140 can by any of the valvular structures described in U.S. Application Publication No. 2011/0118766 A1 (for example, FIGS. 10A-11C, 40G, 56A-56D and FIGS. 57A-57D), which is incorporated herein for all purposes by reference.

After the valvular structure 140 is removed from attachment ring 30, cannula 158 is pushed down until it contacts attachment ring 30. Securement member 162 is secured to attachment ring 30 so as to form a liquid-tight seal with attachment ring 30. Attachment can be accomplished with a press-fit, a resilient gasket, helical screw threads, interlocking/mating features, mechanical fasters or a combination thereof on either one or both of securement member 162 and attachment ring 30. After attachment of securement member 162 on attachment ring 30, plug 164 can be removed and fluid conduit 166 can be attached to cannula 158 by any suitable method. Examples of suitable methods include clamping, suturing, helical screw threads, interlocking/mating features, mechanical fasters or a combination thereof. Fluid conduit 166 can be a vascular graft, an anatomical lumen, a fluid connection to a VAD, or other tubular structure depending on the type of surgical procedure being performed.

Figure 26:
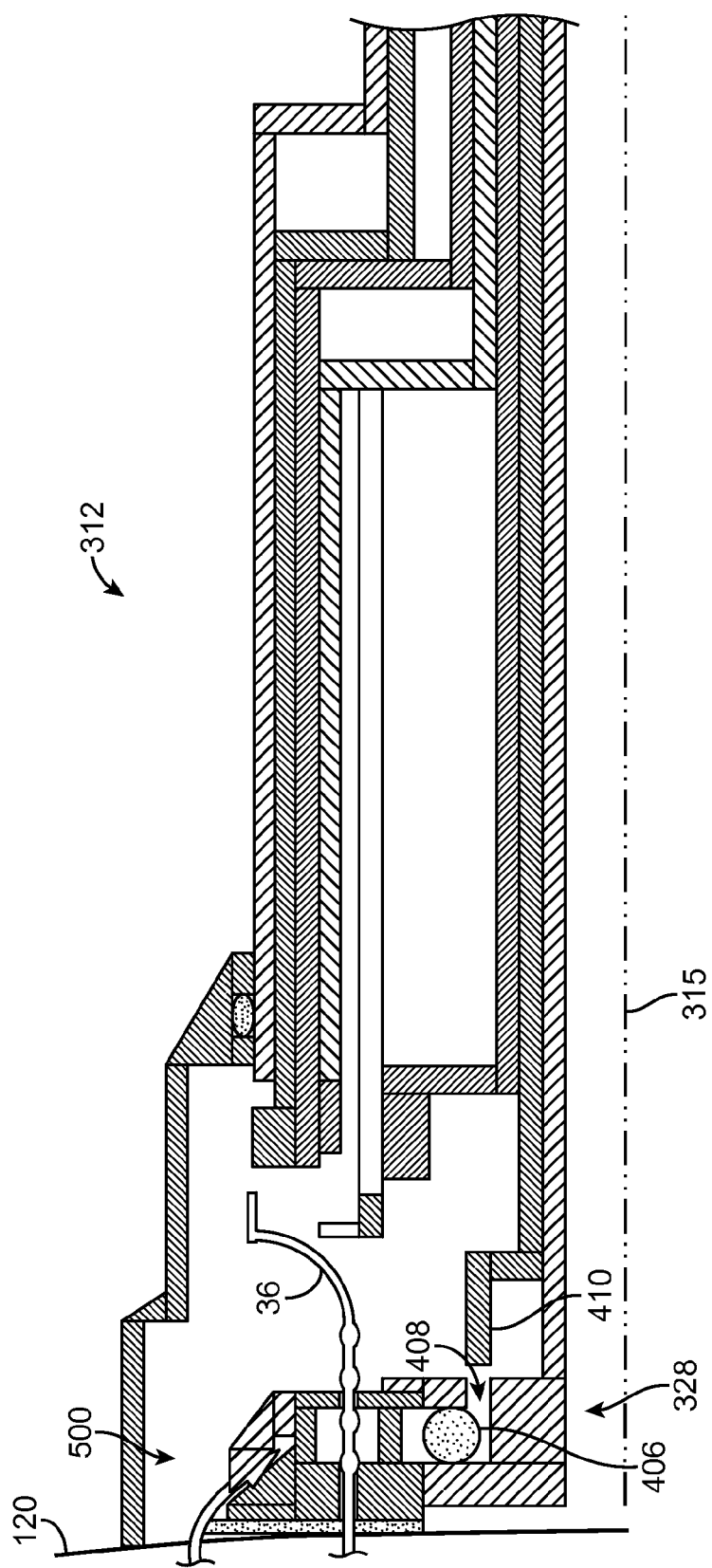
Figure 27:
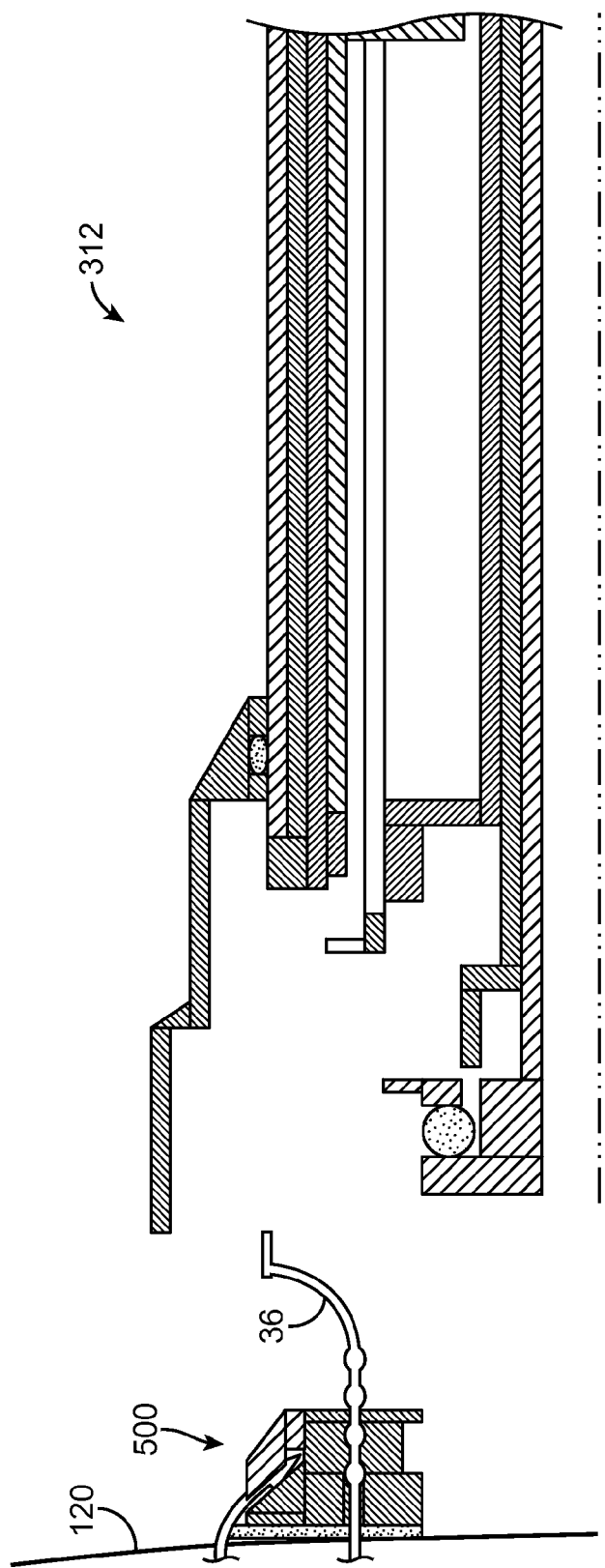
Figure 28:
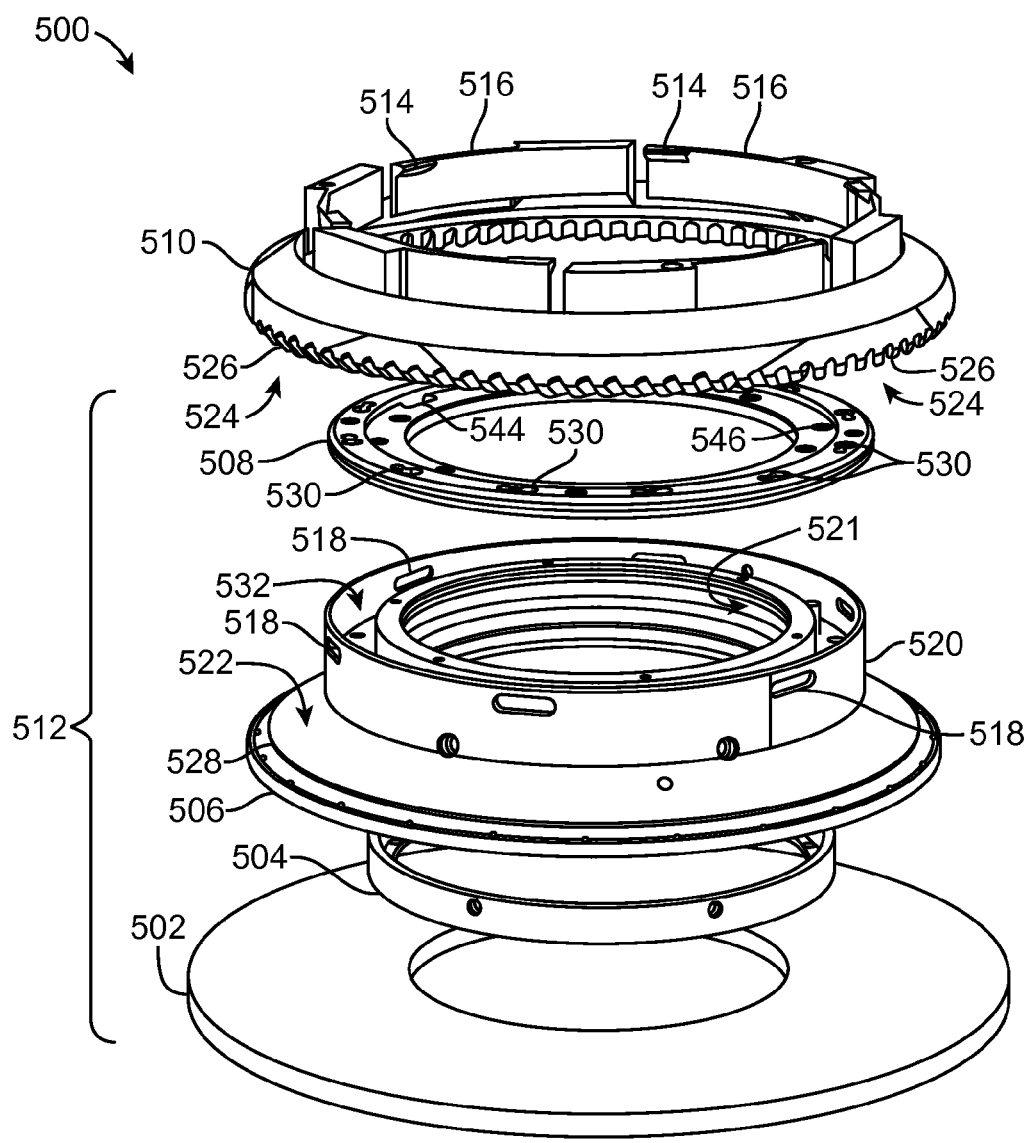
FIGS. 28-30 are exploded and assembled views of exemplary attachment rings that can be mounted on biological tissue using the applicator tool of FIGS. 16-19.
Figure 29:
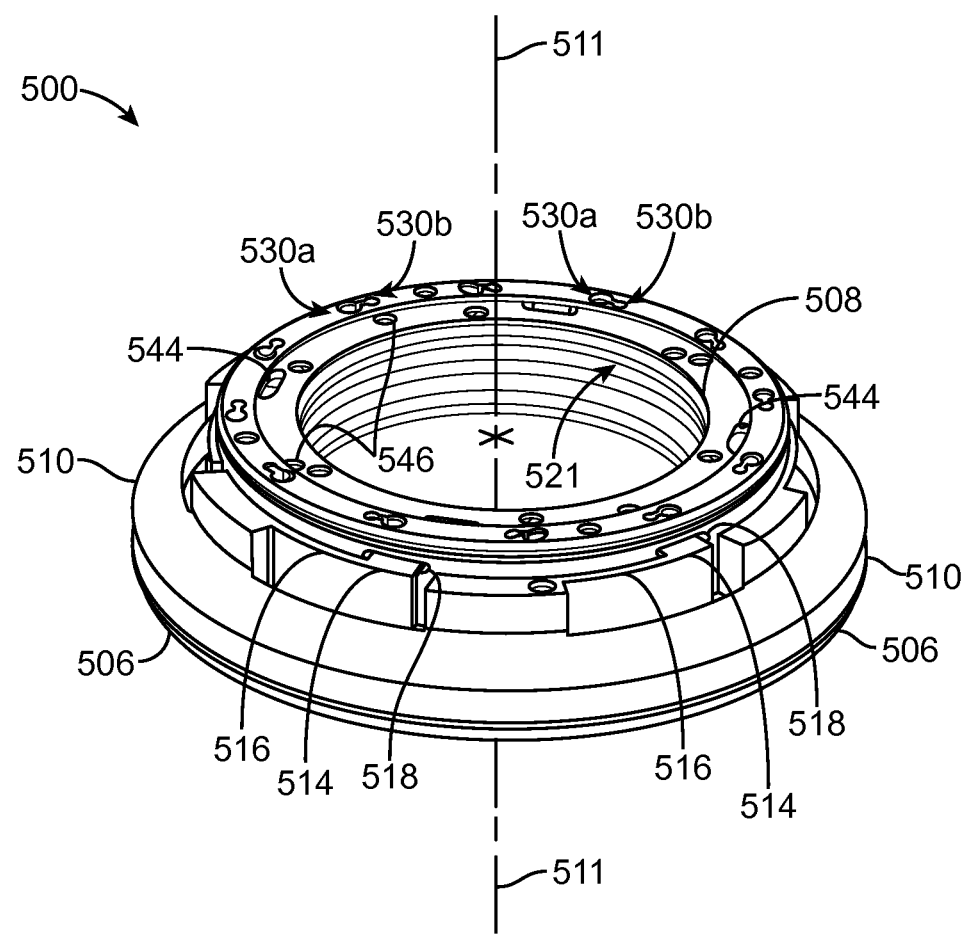
Figure 30:
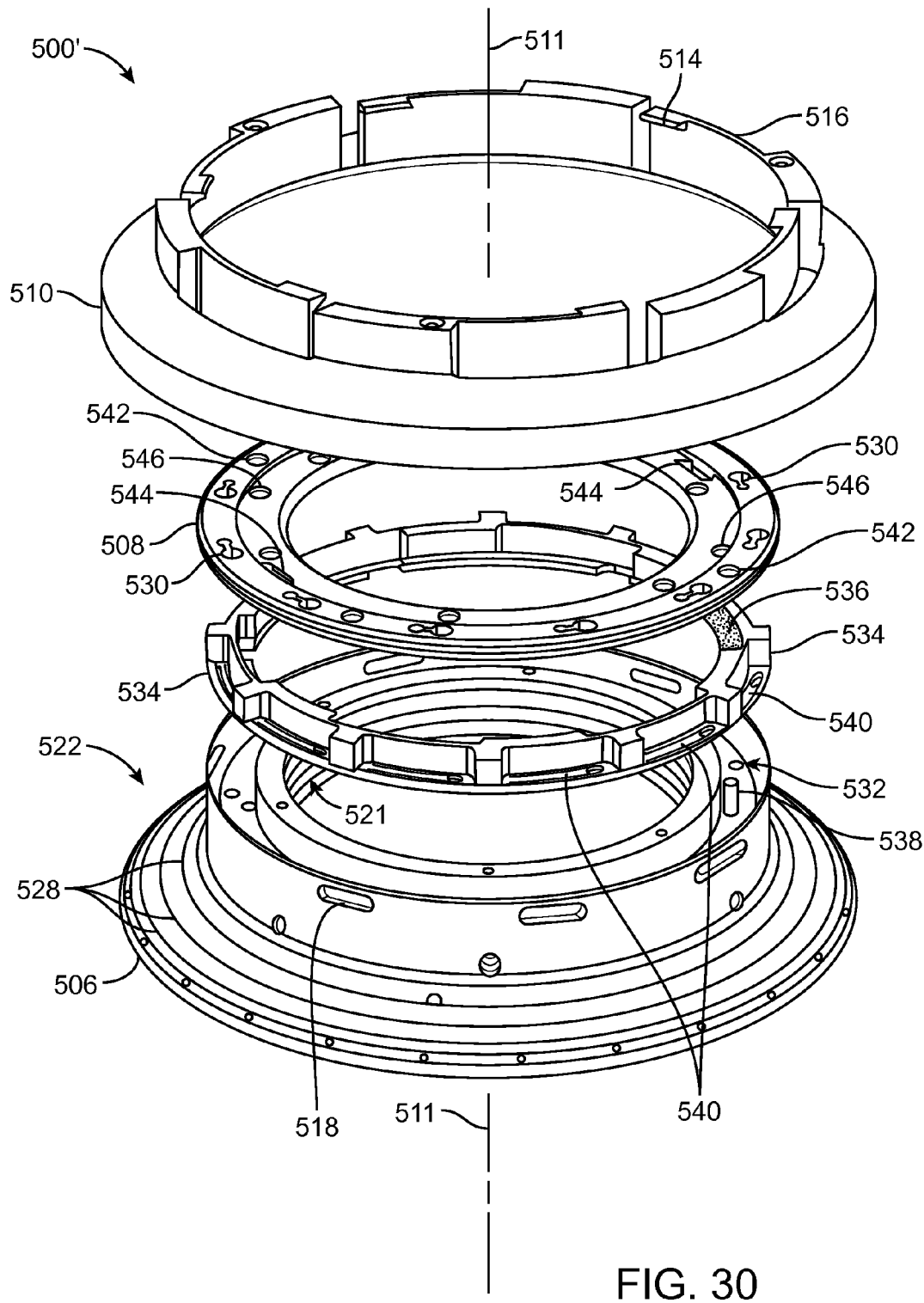

FIGS. 16-27 show exemplary applicator tool 310 for anchoring attachment ring 500 of FIGS. 28-30 to biological tissue. Attachment ring 500 is a type of prosthesis suitable for implantation within a human or animal body. Applicator tool 310 includes forward segment 312 and rear segment 314. Forward segment 312 is configured to carry attachment ring 500 to a desired location on biological tissue. Rear segment 314 includes grip 316 and contains various controls to be manipulated by a person. Axial center line 315 extends axially through the center of forward segment 312.

As used in connection with applicator tool 310, "forward direction" is a direction generally parallel to arrow 317 on axial center line 315, "rearward direction" is a direction generally parallel to arrow 319 on axial center line 315, and "radial direction" is a direction generally perpendicular to axial center line 315.

When a user actuates deployment handle 318, clips 36 are pushed out of applicator tool 310 and into attachment ring 500 and biological tissue. Due to shape memory and/or elasticity of clips 36, tip 44 of each clip follows a loop or curved trajectory in which tip 44 initially travels in a forward direction, then away from attachment ring 500, and then returns toward attachment ring 500. Continuous actuation of deployment handle 318 moves clamp pusher 326 in a forward direction within forward segment 312 of applicator tool 310 for pushing each clip out of the applicator tool 310. When moved forward, clamp pusher 326 (also referred to as a clamping tube) causes a portion of attachment ring 500 to clamp down on and/or trap tips 44 of clips 36.

After tips 44 of clip 36 are trapped within attachment ring 500 and when the user actuates cinching handle 322, catch 46 of all clips 36 are pulled by applicator tool 310 in a rearward direction away from attachment ring 500, causing clips 36 to cinch or to tighten whereby any slack or excess length of clips 36 below biological tissue is reduced.

In other embodiments, the clips 36 are cinched by pulling catch 46 in a circumferential direction within attachment ring 500 instead of pulling catch 46 in a rearward, vertical direction away from attachment ring 500.

After clips 36 are cinched or tightened, the user actuates disengagement knob 324. As a result, connector mechanism 328 is moved to an unlocked position which allows applicator tool 310 and attachment ring 500 to disengage and be pulled apart from each other. After disengagement, attachment ring 500 remains attached to biological tissue by clips 36.

As indicated above, applicator tool 310 is used to carry attachment ring 500 to a desired location on biological tissue. FIGS. 16-20 show applicator tool 310 without attachment ring 500. FIGS. 21-26 show applicator tool 310 with attachment ring 500.

As shown in the dissembled view of FIG. 28, attachment ring 500 comprises flexible cuff 502, bottom mount 504 (also called a base), main body 506 (also called a ring body), top plate 508 (also called a cinch plate), and clamping ring 510. Flexible cuff 502, bottom mount 504, main body 506, top plate 508, and clamping ring 510 are each ring-shaped and are, in some embodiments, rotationally symmetrical about axial centerline 511. When assembled for use with applicator tool 310, cuff has been secured to mount 504 with sutures, adhesive and/or other attachment methods known in the art. Also, bottom mount 504, main body 506 and top plate 508 have been secured to each other with screws, mechanical clips, adhesive and/or other attachment methods known in the art. In some embodiments, at least bottom mount 504 and/or top plate 508 are an integral part of main body 506. Cuff 502, mount 504, main body 506, and top plate 506 collectively form ring assembly 512.

During use within a patient, connector mechanism 328 (FIG. 21) of applicator tool 310 retains ring assembly 512 while clamp pusher 326 (FIG. 21) pushes clamping ring 510 onto ring assembly 512. Clamping ring 510 includes a plurality of cantilevered and flexible arms 516. Ramped catch members 514 protrude radially inward from flexible arms 516 and are configured to enter into and engage lock feature 518 on an exterior surface 520 of main body 506. Lock feature 518 is in the form of a depression or recess in exterior surface 520.

Figure 17:
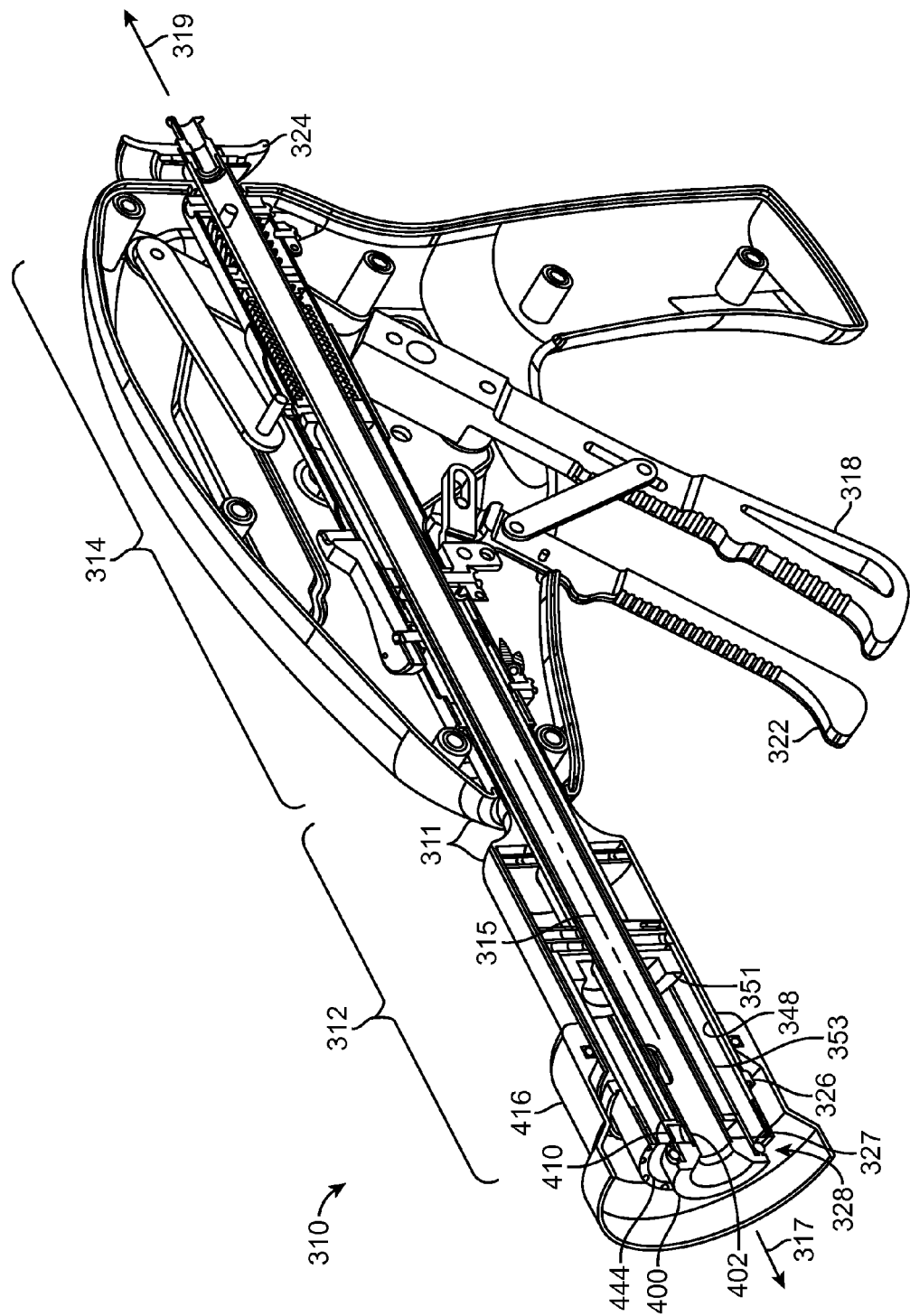
Figure 18:
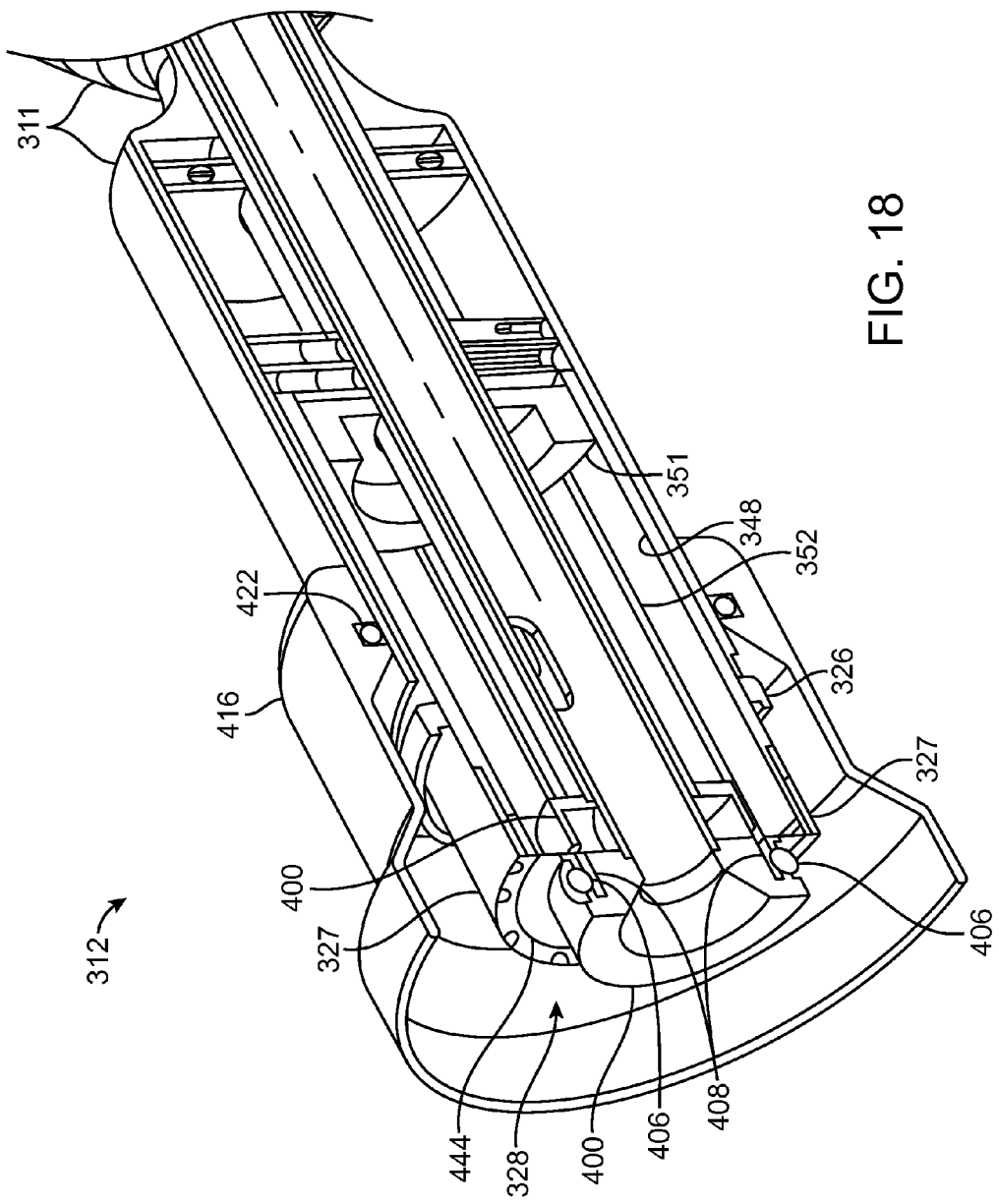
Figure 19:
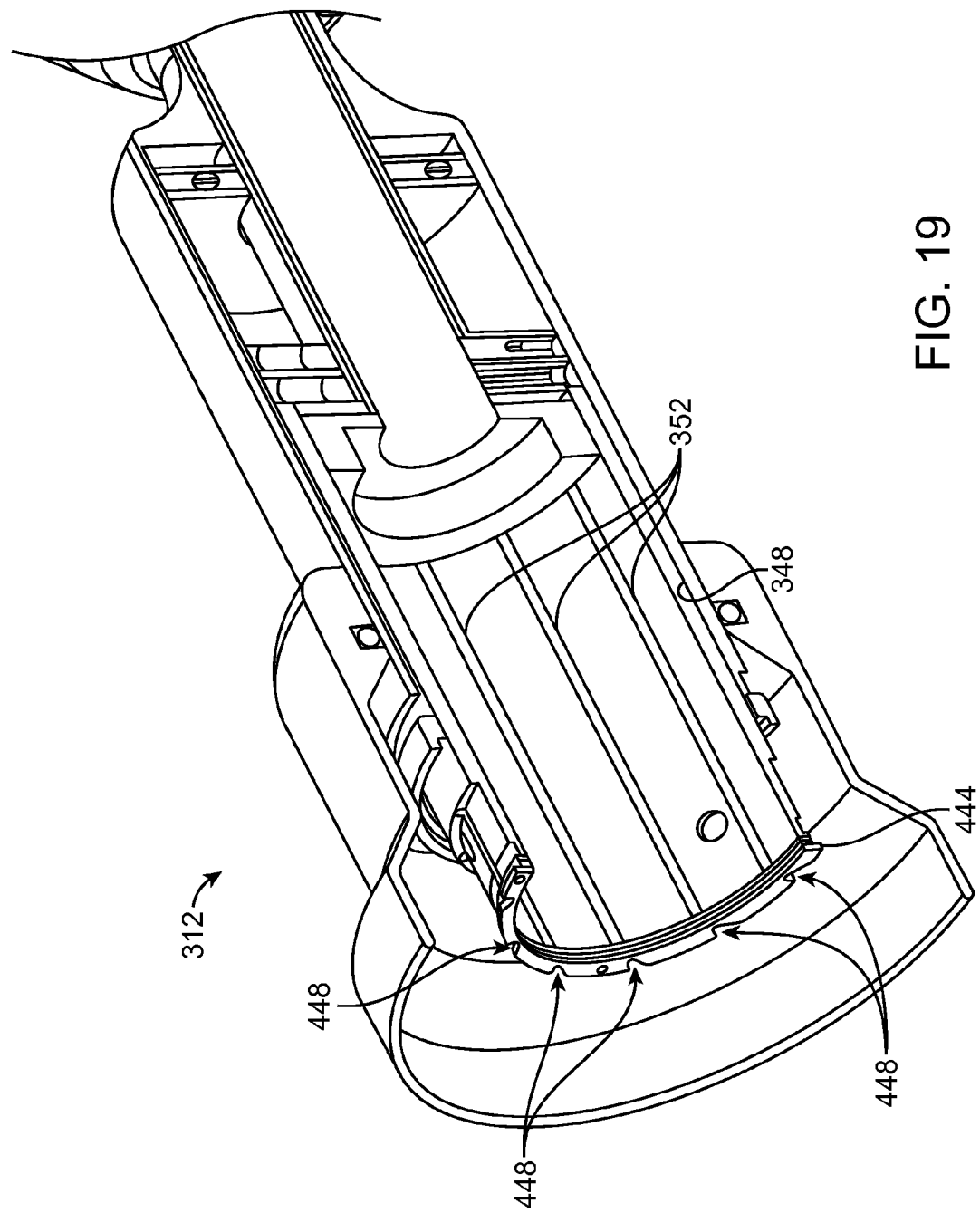
FIG. 19 is a detailed cutaway view of the applicator tool of FIG. 18 with some parts absent from the illustration to more clearly show other parts.

FIGS. 17 and 18 show applicator tool 310 with connector mechanism 328 in an unlocked position. FIG. 19 shows applicator tool 310 illustrated without connector mechanism 328 to more clearly show other components of applicator tool 310. FIGS. 20-27 show a partial cross-sectional view of forward segment 312 of applicator tool 310, with only the structures above axial center line 315 shown for ease of illustration. Forward segment 312 is substantially symmetrical about axial center line 315. It is to be understood that that structures below axial center line 315, are present although not illustrated or shown, are substantially the same as the structures above axial center line 315.

Figure 20:
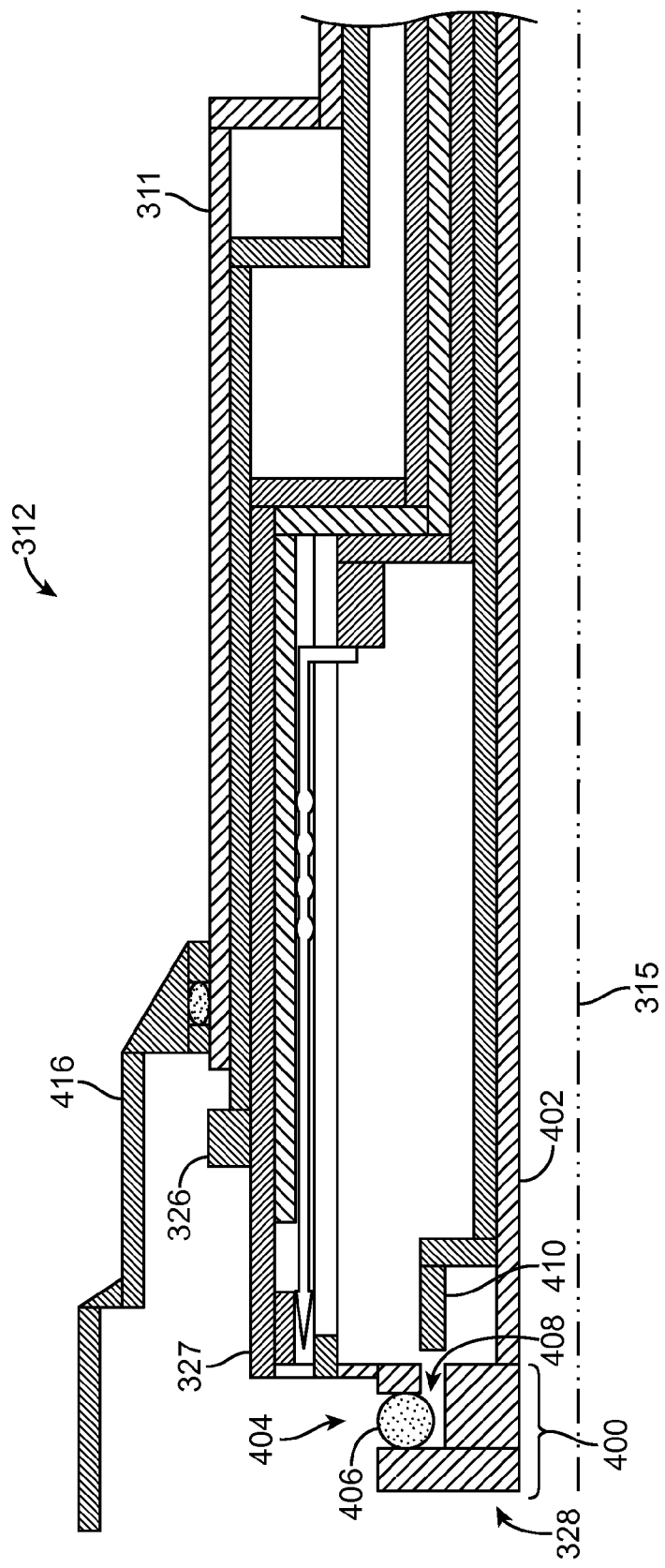
FIG. 20-27 are partial sectional views of the applicator tool of FIGS. 16-19, showing sequential operation of the applicator tool for deploying and cinching a plurality of clips.

Features of connector mechanism 328 are shown in FIGS. 18 and 20. A plurality of first lock elements 406 are carried within connector ring 400 of connector mechanism 328. Second lock element 410 is controlled by disengagement knob 324 (FIG. 16) and causes first lock elements 406 to move from a disengaged position (FIG. 20), in which the first lock element is contained entirely within connector ring 400, to an engaged position (FIG. 21), in which first lock element protrudes out of connector ring 400. When in the engagement position, first lock elements 406 retain ring assembly 512 onto applicator tool 510.

As described below, a method for connecting a conduit to tissue can include (1) mounting attachment ring 500 to applicator tool 310; (2) moving applicator tool 310 with the mounted attachment ring 500 to place attachment ring 500 in contact with biological tissue; (3) deploying clips 36 out of applicator tool 310 and through both attachment ring 500 and biological tissue; (4) clamping and/or trapping tips 44 of clips 36 after penetration through the biological tissue on attachment ring 500; (5) cinching clips 36 by pulling catch 46 of clips 36 away from attachment ring 500 and biological tissue; (6) releasing clips 36 from applicator tool 310; and (7) releasing attachment ring 500 from applicator tool 310.

Figure 21:
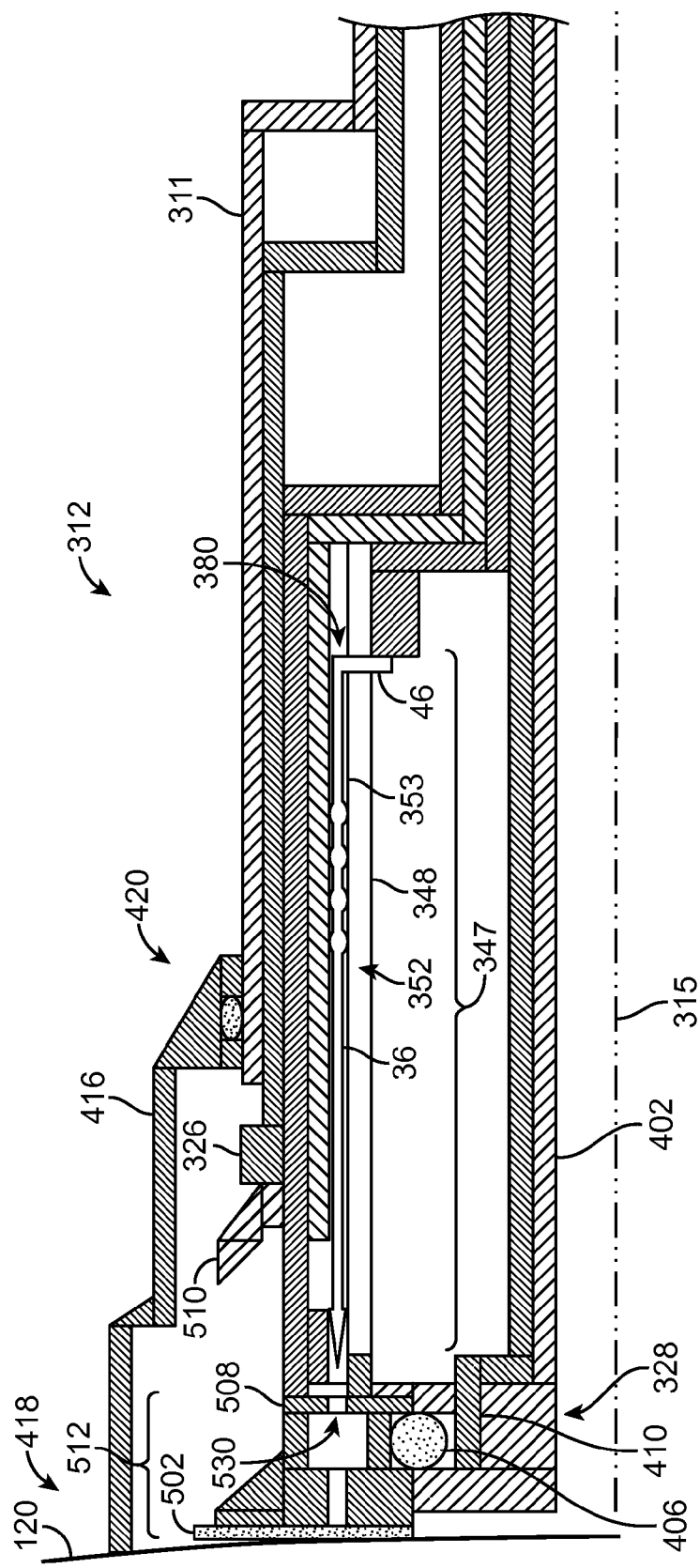

FIG. 21 shows attachment ring 500 mounted to forward segment 312 of applicator tool 310 and placed in contact with top surface 120 biological tissue. Connector mechanism 328 temporarily retains ring assembly 512 of attachment ring 500. Second lock element 410 keeps first lock element 406 at the engaged position so that first lock element 406 protrudes into and engages internal annular groove 521 (FIGS. 28 and 29) formed in an interior surface of ring assembly 512. Clamping ring 510 of attachment ring 500 is temporarily retained at a location adjacent clamp pusher 326. Applicator tool 310 is positioned by the user so that cuff 502 and suction cap 416 make contact with top surface 120 of biological tissue.

Suction cap 416 is configured to maintain suction over top surface 120 of biological tissue. Suction cap 416 is tubular in shape and comprises forward end 418 and rear end 420. Rear end 420 is slideably coupled to applicator tool body 311. Suction cap 416 contains resilient O-ring gasket 422 adjacent rear end 420. O-ring gasket 422 maintains a substantially fluid-tight seal between suction cap 416 and applicator tool body 311. In use, forward end 418 of suction cap 416 is placed over the surface 120 of a target site on the biological tissue, then the user can apply a vacuum or suction through hollow shaft 402 to prevent relative movement between the biological tissue and the cuff 502 of attachment ring 500 during deployment of clips 36 into the biological tissue. To accommodate a variety of possible curvatures in the biological tissue, the user may slide suction cap 416 in a forward or rearward direction relative to applicator tool body 311 so that cuff 502 of attachment ring 500 and forward end 418 of suction cap 416 simultaneously contact top surface 120 of biological tissue.

Suction cap 416 ensures the good contact between the applicator tool and the biological tissue. Suction cap 416 ensures that the deployment site is clear of external elements. Suction cap 416 deforms the tissue to more ideal deployment shape. Suction cap 416 reduces the movement of the tissue relative to the applicator tool.

Still referring to FIG. 21, clip 36 is contained in clip holder 347 of clip tube 348. Although one clip is illustrated, clip tube 348 can include any number of clip holders 347 and clips 36. Clip holder 347 includes clip groove 352 having axial slot opening 353 and bottom portion 380. Catch 46 of clip 36 protrudes out of axial slot opening 353. The remainder of clip 36 is retained in bottom portion 380 of clip groove 352 since axial slot opening 353 is narrower in width than clip 36 except for catch 46. Clip pusher surface 351 abuts catch 46.

Figure 22:
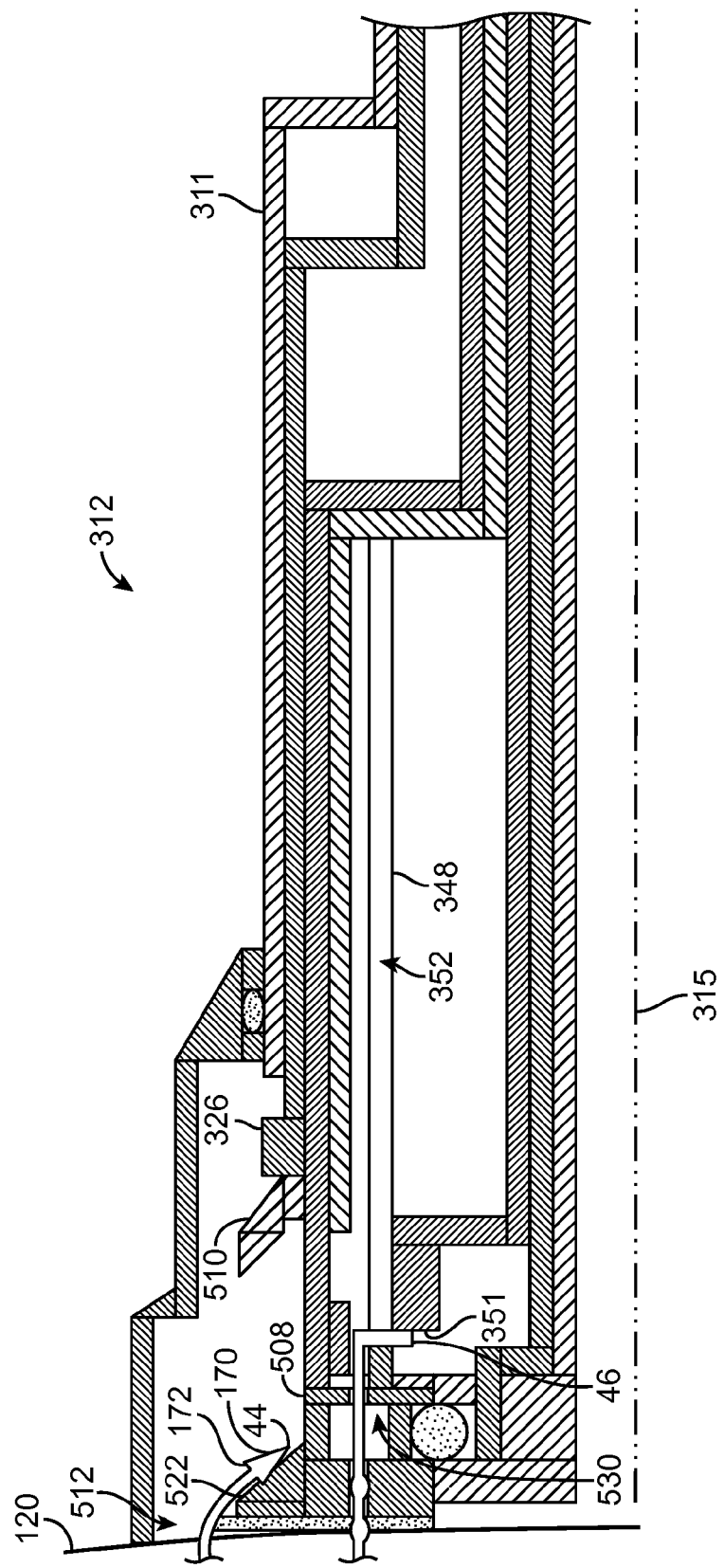

FIG. 22 shows clip 36 deployed out of the forward opening of clip groove 352 after catch 46 of clip 36 has been pushed in a forward direction by clip pusher surface 351. Barbed head 170 of clip 36 has passed through ring assembly 512, into and out of biological tissue, and onto clamp surface 522 of ring assembly 512. Clip 36 extends through peripheral through-hole 530 formed into top plate 508 of ring assembly 512.

Figure 23:
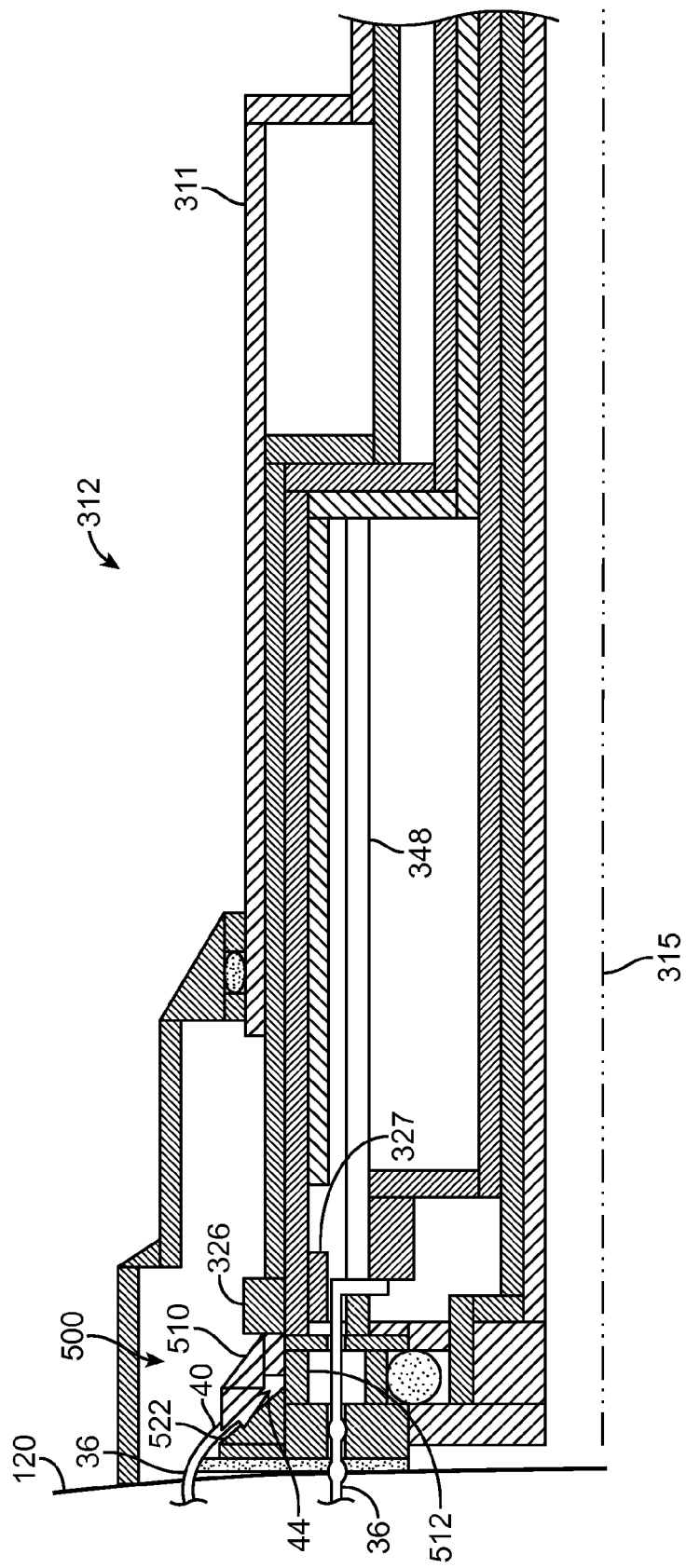

FIG. 23 shows tip 44 of clip 36 clamped and/or trapped by attachment ring 500 after clamping ring 510 has been pushed from its initial position (FIG. 24) by clamp pusher 326. Tip 44 is retained between clamping ring 510 and clamp surface 522 of attachment ring 500. Forward segment 40 of clip 36 passes through one of the plurality of grooves 524 (FIG. 28) formed in a forward facing surface of clamping ring 510. Grooves 524 are at least as wide as forward segment 40 of clip 36 and are narrower in width than base 172 (FIG. 20) of barbed head 170 on clip 36. Ridges 526 (FIG. 28) on each side of groove 524 engage base 172 of clip 36. In some embodiments, attachment ring 500' (FIG. 30) has no grooves 524, and tip 44 is retained by other types of grooves, by pressure and/or by other features.

In some embodiments, clamp surface 522 includes annular groove 528 (FIG. 28) configured to engage base 172 of barbed head 170 on clip 36. In other embodiments, clamp surface 522 includes a plurality of concentric annular grooves 528 (FIG. 30).

Figure 24:
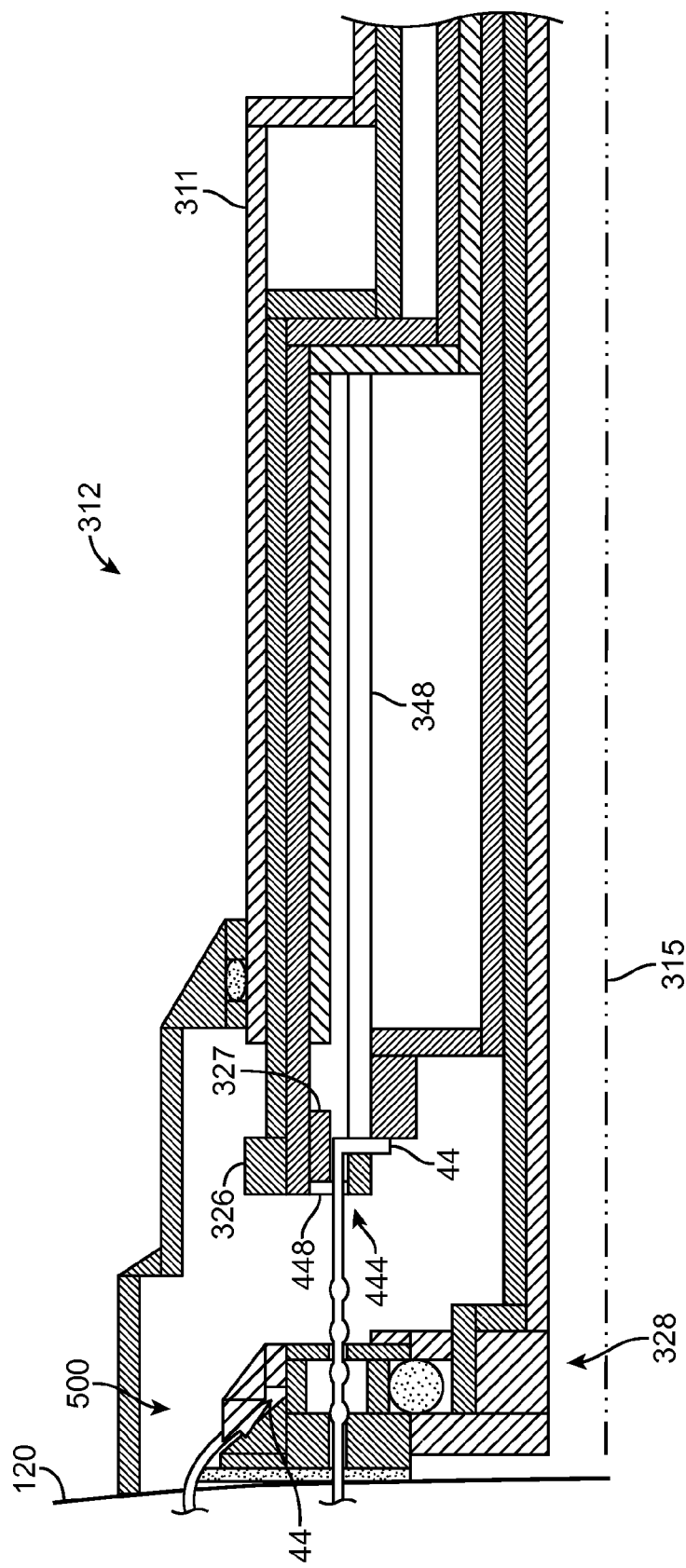

FIG. 24 shows clip 36 after it has been cinched or tightened. Catch 46 of clip 36 has been pulled in a rearward direction while tip 44 of clip 36 is trapped within attachment ring 500. Catch 46 is pulled rearward by cinching ring 444 which is fixedly attached to or is an integral part of clip tube 348.

Figure 25:
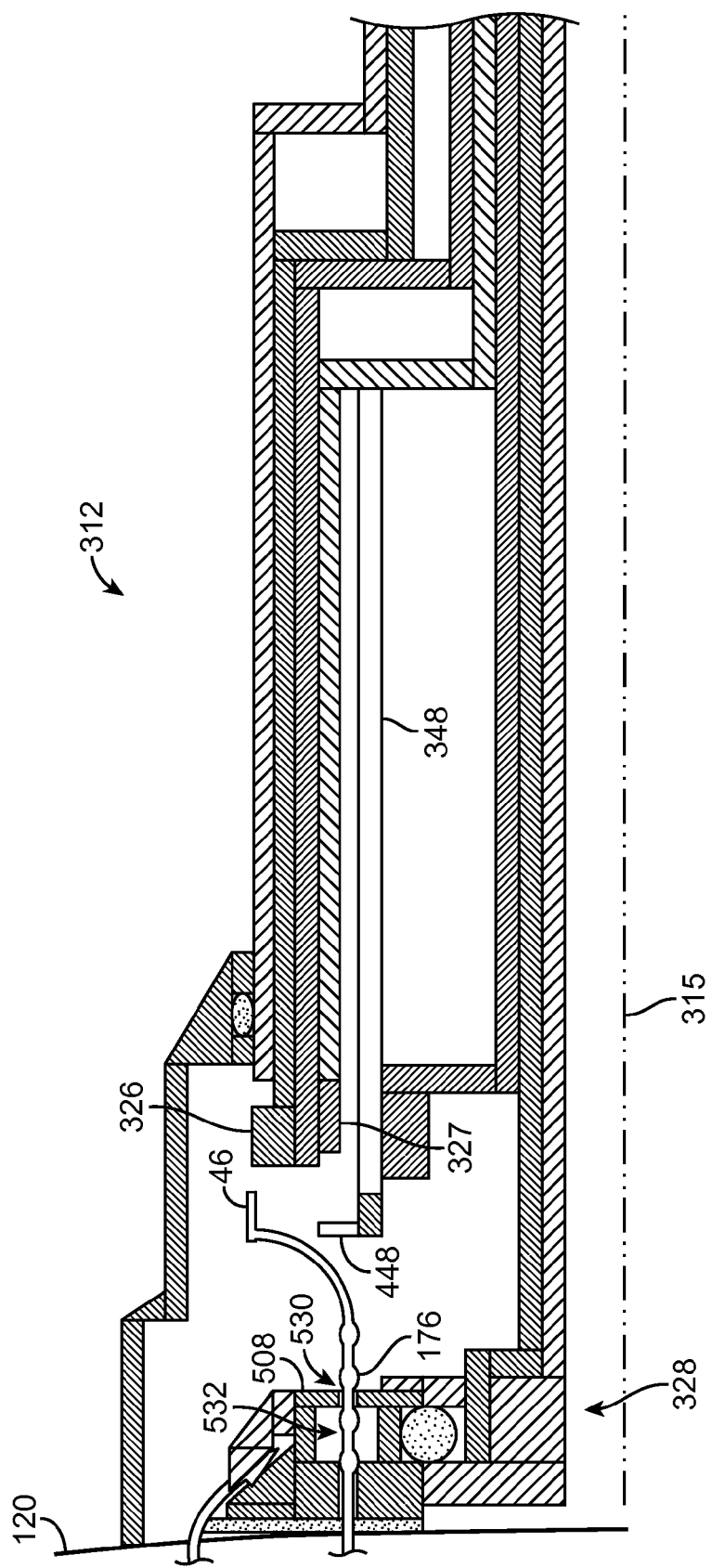

FIG. 25 shows clip 36 after it has been released from applicator tool 310. Movable barrier 327 has moved in a rearward direction away from cinching ring 444 so as to uncover the exit opening of radial cut 448 formed through cinching ring 444. Due to its shape memory and/or elasticity, clip 36 has a natural tendency to autonomously move to a curved configuration from a straight configuration. Thus, when movable barrier 327 moves away from exit opening of radial cut 448, the shape memory and/or elasticity causes rear segment 42 and catch 46 of clip 36 autonomously pass out of the exit opening of radial cut 448 and become detached from applicator tool 310. The ability of clip 36 to pass out of radial cut 448 is evident from FIG. 19 in which movable barrier 327 is absent from the illustration. After its release, the rear segment of clip 36 is prevented by top plate 508 from moving in toward top surface 120 of biological tissue. Top plate 508 engages bumps 176 of clip 36.

After cinching and release of clip 36 and in order to prevent subsequent loosening of clip 36, engagement between attachment ring 500 and bumps 176 of clip 36 can be the result of (1) the shape memory and/or elasticity of clip 36, (2) one or more elements within attachment ring 500, or (3) a combination thereof.

In FIG. 29 peripheral through-holes 530 of top plate 508 are key-hole in shape. As shown in FIG. 29, key-hole shaped through-holes 530 have wide area 530a and narrow area 530b. Wide area 530 is sized to receive barbed head 170 and bumps 176 of clip 36. Bumps 176 are unable to pass through narrow area 530a. Narrow area 530a is sized to receive wire body 38 (FIGS. 3A and 4) of clip 36. In some embodiments, the shape memory and/or elasticity of clip 36 causes clip medial segment 174 (FIGS. 3A and 4) to bend autonomously and move from wide area 530a toward narrow area 530b of through-holes 530. This movement helps bumps 176 engage top plate 508 of attachment ring 500 and prevent clip 36 from loosening after being cinched. Attachment ring 500 includes chamber 532 (FIG. 28) enclosed by top plate 508 and main body 506. Chamber 532 can be sized to allow clip 36 to bend autonomously after being released from applicator tool 310 so that bumps 176 engage top plate 508.

In FIG. 30, attachment ring 500' can include annular element 534 that is movable within annular chamber 532 of main body 506 for preventing loosening of clip 36 after the clip is cinched. Compression spring 536 is disposed between movable element 534 and post 538 of main body 506. Spring 536 pushes and biases movable element 534 to move toward an engaged orientation at which movable element 534 restricts a passageway through which clip 36 passes when clip 36 is deployed through attachment ring 500'. Though one spring 536 and post 538 is illustrated, there can be a plurality of springs and posts to provide a greater amount of force on movable element 534. At the engaged orientation, movable element 534 limits bumps 176 of clip 36 to one-way movement through the restricted passageway. At the engaged orientation, movable element 534 allows movement of bumps 176 in a rearward direction (away from the biological tissue) during cinching of clip 36 by applicator tool 310, and prevents movement of bumps 176 in a forward direction (toward the biological tissue) after release of clip 36 from applicator tool 310. Element 534 includes a plurality of leaf springs 540. The one-way movement is provided by leaf springs 540 which restrict the clip passageway. Each clip 36 is acted upon by one leaf spring 540. Each leaf spring 540 abuts a surface of chamber 532 in main body 506. Each leaf spring 540 is configured to move in a rearward direction and is prevented from moving in a forward direction due to contact with main body 506. Prior to and during deployment of clip 36 through attachment ring 500', movable element 534 is held in a disengaged orientation at which movable element 534 does not restrict the passageway through which clip 36 passes. Movable element 534 is held in the disengaged orientation, against spring 536, by restraining pins that pass through axial apertures 542 in top plate 508. The restraining pins abut and keep movable element 534 in the disengaged orientation until the restraining pins are pulled out of axial apertures 542. In some embodiments, the restraining pins can be fixedly attached to or form an integral part of clip tube 348 of applicator tool 310. Restraining pins are pulled out of axial apertures 542 when clip tube 348 is retracted in a rearward direction during the process of cinching of clip 36 (such as in FIG. 24), thereby allowing movable element 534 to move to its engaged orientation before clip 36 is released from applicator tool 310.

FIG. 26 shows connector mechanism 328 of applicator tool 310 in an unlocked position after a user has pulled disengagement knob 324 (FIG. 17) in a rearward direction. Second lock element 410 has moved out of axial aperture 408, which allows first lock element 406 to move to its disengaged position (FIG. 26) from its engaged position (FIG. 25). With first lock element 406 is at its disengaged position, forward segment 312 of applicator tool 310 can be lifted away from attachment ring 500 and top surface 120 of biological tissue, as shown in FIG. 27.

After applicator tool 310 is separated from attachment ring 500, the method can proceed in the same or similar manner as was described in connection with FIGS. 11-15. For example, the method can include: temporarily mounting valvular structure 140 on attachment ring 500; using instrument 150 to make a circular through-hole in biological tissue; inserting cannula 158, or other tubular structure, through valvular structure 140, attachment ring 500, and the through-hole in biological tissue; and attaching fluid conduit 166 to cannula 158.

Figure 33:
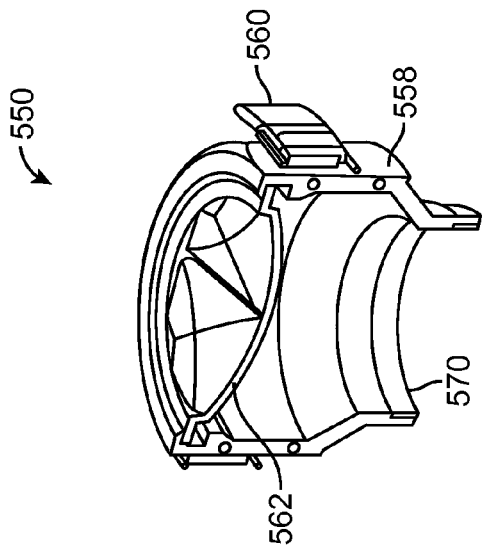
FIGS. 31-33 are perspective, detailed perspective, and perspective cutaway views of a valvular structure that can be mounted on the attachment rings herein.
Figure 32:
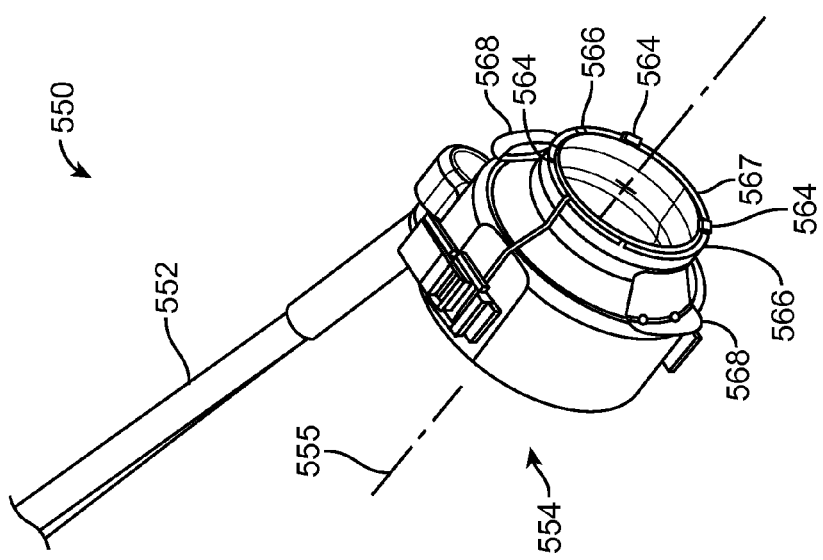
Figure 31:
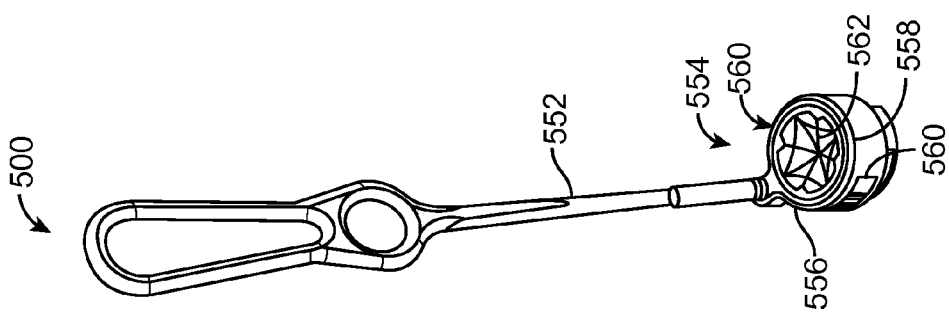

The valvular structure in the above describe methods can be as shown in FIGS. 31-33. Alternative valvular structure 550 of FIGS. 31-33 is configured to perform the same or similar function as valvular structure 140 of FIGS. 11-14. Alternative valvular structure 550 is configured to receive instrument 150 of FIG. 12. Alternative valvular structure 550 includes an integrated handle 552, so clamp 130 of FIG. 11 is not necessary to hold alternative valvular structure 550. Handle 552 is fixedly attached to housing 554. Housing 554 includes housing first portion 556 and housing second portion 558 that are configured to be selectively locked together and moved apart from each other. First housing portion 556 is temporarily connected to second housing portion 558 by movable lock members 560. Lock members 560 have a locked orientation in which lock members 560 keep first housing portion 556 and second housing portion 558 in fluid-tight sealing engagement with each other. A user may move lock members 560 to an unlocked orientation in which first housing portion 556 and second housing portion 558 can be disengaged from other. Housing 554 contains valve 562, which can have the same or similar configuration as valve 154 of FIG. 11. Valve 562 can have the same or similar configuration as quadcuspid valves, bicuspid valves, dome valve, or diaphragm valve described in U.S. Application Publication No. 2011/0118766 A1.

As shown in FIG. 32, the bottom or forward edge 567 of housing 554 includes a plurality of L-shaped hook members 564 configured to enter and engage elongate slots 544 (FIGS. 28-30) in top plate 508 of attachment ring 500 and 500'. After hook members 564 enter elongate slots 544, rotation of housing 554 about its central axis 555 causes hook members 564 to engage top plate 508 and thereby lock alternative valvular structure 550 onto the attachment ring 500 or 500'. Subsequent rotation of housing 554 in the opposite direction allows causes hook members 564 to disengage top plate 508 and thereby allow valvular structure 550 to detach from attachment ring 500 or 500'.

As shown in FIG. 32, the bottom or forward edge 567 of housing 554 includes a plurality of movable lock pins 566 configured to engage lock recesses 546 (FIGS. 28-30) in top plate 508 of attachment ring 500 and 500'. When housing 554 is rotated about its central axis 555, lock pins 566 enter lock recesses 546 when hook members 564 have engaged top plate 508. With lock pins 566 in lock recesses 546, rotation of housing 554 in the opposite direction is prevented, which also prevents alternative valvular structure 550 from detaching from attachment ring 500 or 500'. Lock pins 566 are spring-loaded or biased to axially protrude in a forward direction from circular edge 567 of housing 554. Lock pins 566 are coupled to release handles 568. When a user moves release handles 568 in a rearward direction, lock pins 566 move in a rearward direction out of lock recesses 546 of attachment ring 500. When lock pins 566 are pulled out of lock recesses 546, the user may rotate housing 554 in the opposite direction and then detach valvular structure 550 from attachment ring 500 or 500'.

Figure 34:
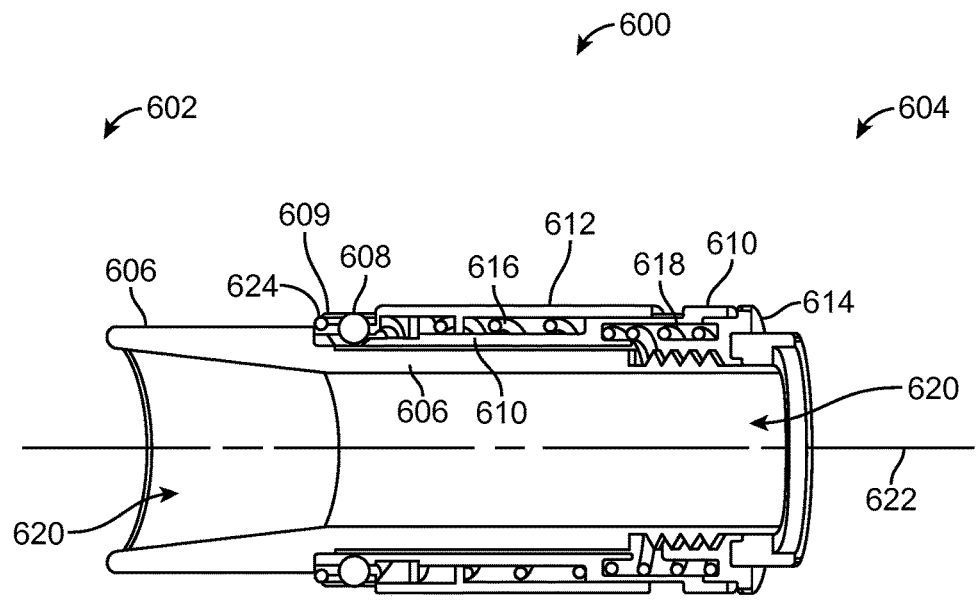
FIGS. 34 and 35 are perspective and perspective cutaway views of an exemplary cannula that can be mounted on the attachment rings herein.
Figure 35:
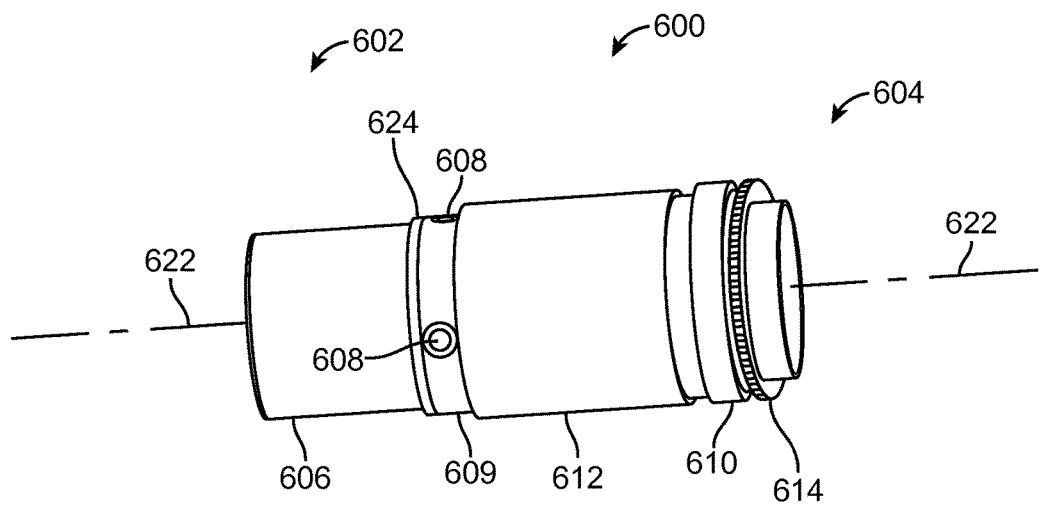

The cannula in the above describe methods can be as shown in FIGS. 34 and 35. Cannula 600 of FIGS. 34 and 35 is configured to perform the same or similar function as cannula 158 of FIGS. 14 and 15. Cannula 600 is a type of prosthesis suitable for implantation within a human or animal body. Cannula 600 can be, in some embodiments, a conduit of a ventricular assist device. Front end 602 of cannula 600 can be inserted through valve 562 (FIG. 31) of valvular structure 550, then into attachment ring 30, 500 or 500', and then into circular through-hole in biological tissue. Thereafter, a conduit can be secured to rear end 604 of cannula 600.

Cannula 600 includes tubular cannula body 606, first lock members 608 in the form of a sphere, ring 609 containing first lock members 608, second lock member 610 in the form of a sleeve, cover sleeve 612, and control member 614 in the form of a rotatable knob. Cannula body 606 includes a non-porous inner surface that defines central fluid passageway 620 from front end 602 to rear end 604. Central axis 622 extends through the center of fluid passageway 620. Each of first lock members 608, ring 609, second lock member 610, cover sleeve 612, and control member 614 extends around central axis 622 and is attached to cannula body 606 at a location outside central fluid passageway 620. Control member 614 and cannula body 606 each have helical threads that mate with each other to allow control member 612 to be selectively positioned in either an axially forward position or an axially rearward position. Control member 614 is illustrated in its rearward position.

First coil spring 616 is contained within a cavity between second lock member 610 and cover sleeve 612. First coil spring 616 pushes cover sleeve 612 in a forward direction toward front end 602, so that cover sleeve 612 covers first lock member 508. Cover sleeve 612 is illustrated in a retracted position after it has been moved in a rearward direction toward rear and 604, so that first lock members 508 are exposed.

Second coil spring 618 is contained within a cavity between second lock member 610 and control member 614. Second coil spring 618 pushes second lock member 610 in a forward direction toward front end 602, so that second lock member 610 is in a lock position between first lock members 608 and cannula body 606. When second lock member 610 is in the lock position, first lock members 608 are forced radially outward through apertures in ring 609. Second lock member 610 is illustrated in a retracted position after it has been moved in a rearward direction, which allows first lock members 608 to move radially inward.

At the start of the process of mounting cannula 600 onto attachment ring 30, 500 or 500', cannula 600 can be held such that second lock member 610 is in its retracted position. For example and not limitation, cannula 600 can be held with a mounting clamp (not illustrated) which pulls second lock member 610 toward control member 614.

While forward end 602 of cannula 600 is moved in a forward direction and enters valvular structure 550, cover sleeve 612 passes through valve 562 and annular gasket 570 (FIG. 33). In some embodiments, annular gasket 570 is configured to provide a fluid-tight seal against the outer surface of cover sleeve 612 and/or against top plate 508 of attachment ring 500 or 500' and/or Interior cylindrical wall 732 (FIG. 2A) of attachment ring main body 70.

While forward end 602 of cannula 600 is moved in a forward direction and enters attachment ring 30, 500 or 500', cover sleeve 612 abuts top plate 508 (FIGS. 29 and 30) and is pushed rearward to its retracted position, so that first lock members 608 become exposed. With second lock member 610 at its retracted position, first lock members 608 are allowed to move radially inward. When they move radially inward, first lock members 608 are able to travel past top plate 508 (FIGS. 29 and 30) of attachment ring 500 or 500' or cinching ring 86 (FIG. 2A) of attachment ring 30, then enter annular groove 521 (FIGS. 30 and 31) or 77 (FIG. 2A) of the attachment ring. Thereafter, second lock member 610 can be released, such as by removing a mounting clamp (not illustrated), so that second coil spring 618 pushes second lock member 610 into the cavity between first lock members 608 and cannula body 606. First lock members 608 are pushed radially outward and become engaged within annular groove 521 (FIGS. 30 and 31) or 77 (FIG. 2A) of the attachment ring, which prevents cannula 550 from separating from the attachment ring. To prevent second lock member 610 from retracting or moving rearward, the user can rotate control member 614 to its forward position where it presses against second lock member 610.

O-ring seal 624 is attached to ring 609 and faces radially outward. O-ring seal 624 is made of an elastic material and is sized and shaped to form a fluid-tight seal with an inner surface of main body 506 (FIGS. 30 and 31) or 70 (FIG. 2A) of the attachment ring. After attachment ring 30, 500 or 500' is secured to biological tissue, the fluid-tight seal substantially prevents a body fluid such as blood from leaking out between cannula 600 and the attachment ring.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method for connecting a prosthesis to tissue, the method comprising:
    placing an attachment ring on the tissue while the attachment ring is mounted on an applicator tool containing a plurality of clips; followed by
    anchoring the attachment ring on the tissue, the anchoring including
    moving a forward segment of each of the clips in a forward direction out of the applicator tool and through the attachment ring and the tissue,
    after the clips are moved through the attachment ring, restraining the clips so that a rear segment of each of the clips are capable of one-way movement for cinching the clips, and
    after the restraining of the clips, pulling the rear segments of the clips while the forward segments of the clips are clamped or trapped by the attachment ring.

2. The method of claim 1, further comprising forming a through-hole in the tissue with an instrument passed through the attachment ring, the forming of the through-hole performed after the anchoring the attachment ring on the tissue.

3. The method of claim 2, further comprising:
    attaching a valvular structure to the attachment ring before the forming of the through-hole in the tissue; and
    inserting an inflow conduit of a ventricular assist device through the attachment ring and the through-hole.

4. The method of claim 1, wherein the moving of the forward segments of the clips includes the applicator tool pushing the rear segments of the clips toward the attachment ring.

5. The method of claim 1, wherein the pulling of the rear segments of the clips causes excess lengths of the clips to pull out of the tissue, and the method further comprises preventing the excess lengths of the clips from returning into the tissue.

6. The method of claim 1, wherein the attachment ring includes a main body and a cinching ring disposed within the main body.

7. The method of claim 6, after the pulling of the rear segments of the clips, the method further comprises detaching the applicator tool from the cinching ring of the attachment ring.

8. The method of claim 6, wherein the pulling of the rear segments of the clips includes rotating the cinching ring in a first rotation direction relative to the main body of the attachment ring while the rear segments of the clips are engaged to the cinching ring, and then preventing the cinching ring from rotating in a second rotation direction opposite the first rotation direction.

9. The method of claim 8, wherein the rotating of the cinching ring in the first direction is performed using the applicator tool, and the preventing of the cinching ring from rotating in the second direction is a result of ratchet engagement between cinching ring and the main body of the attachment ring.

10. The method of claim 6, wherein the pulling of the rear segments of the clips includes lifting the cinching ring away from the tissue while the rear segments of the clips are engaged to the cinching ring, and then preventing the cinching ring from lowering toward the tissue.

11. The method of claim 10, wherein the lifting of the cinching ring is performed using the applicator tool, and the preventing of the cinching ring from lowering is a result of ratchet engagement between cinching ring and the main body of the attachment ring.

12. The method of claim 1, wherein the attachment ring includes through-holes in which the clips are located due to the movement of the forward segments of the clips in the forward direction out of the applicator tool, and the applicator tool includes a cinching ring that holds the rear segments of the clips after the movement of the forward segments of the clips in the forward direction out of the applicator tool.

13. The method of claim 12, after the pulling of the rear segments of the clips, the method further comprises detaching the applicator tool from the attachment ring while the cinching ring remains attached to other parts of the applicator tool.

14. The method of claim 12, wherein the pulling of the rear segments of the clips includes preventing the rear segments of the clips from exiting the cinching ring of the applicator tool while lifting the cinching ring away from the tissue, and the lifting causes excess lengths of the clips to pull out of the tissue.

15. The method of claim 14, after the excess lengths of the clips have pulled out of the tissue, the method further comprises releasing the rear segments of the clips from the cinching ring of the applicator tool, and then preventing the excess lengths of the clips from returning into the tissue.

16. The method of claim 15, wherein the preventing of excess lengths of the clips from returning into the tissue is a result of engagement between the rear segments of the clips with the through-holes in the attachment ring.

17. A method for connecting a prosthesis to tissue, the method comprising:
  placing an attachment ring on the tissue while the attachment ring is mounted on an applicator tool containing a plurality of clips; followed by
  anchoring the attachment ring on the tissue, the anchoring including
    moving a forward segment of each of the clips in a forward direction out of the applicator tool and through the attachment ring and the tissue, and
    after the clips are moved through the attachment ring, restraining the clips so that a rear segment of each of the clips are capable of one-way movement for cinching the clips,
  wherein the attachment ring includes a main body and a clamping ring disposed around the main body, the restraining of the clips includes clamping or trapping the forward segments of the clips between the clamping ring and the main body, and the clamping or trapping is performed after the forward segment has traveled out of the tissue subsequent to the forward segment having moved through the attachment ring and the tissue.

* * * * *